(12) United States Patent
Kim et al.

(10) Patent No.: US 12,357,175 B2
(45) Date of Patent: Jul. 15, 2025

(54) METHOD AND APPARATUS FOR STEREOSCOPIC COLOR EYE IMAGING

(71) Applicant: Topcon Corporation, Tokyo (JP)

(72) Inventors: Jongsik Kim, Fort Lee, NJ (US); Dawei Li, Oakland, NJ (US); Toshihiro Mino, Oakland, NJ (US); Zhenguo Wang, Ridgewood, NJ (US); Kinpui Chan, Ridgewood, NJ (US)

(73) Assignee: TOPCON CORPORATION, Tokyo (JP)

( * ) Notice: Subject to any disclaimer, the term of this patent is extended or adjusted under 35 U.S.C. 154(b) by 528 days.

(21) Appl. No.: 17/642,236

(22) PCT Filed: Sep. 10, 2020

(86) PCT No.: PCT/JP2020/034225
§ 371 (c)(1),
(2) Date: Mar. 11, 2022

(87) PCT Pub. No.: WO2021/049558
PCT Pub. Date: Mar. 18, 2021

(65) Prior Publication Data
US 2022/0313084 A1 Oct. 6, 2022

Related U.S. Application Data

(60) Provisional application No. 62/898,812, filed on Sep. 11, 2019.

(51) Int. Cl.
*A61B 3/14* (2006.01)
*A61B 3/00* (2006.01)
*A61B 3/12* (2006.01)

(52) U.S. Cl.
CPC .............. *A61B 3/14* (2013.01); *A61B 3/0008* (2013.01); *A61B 3/12* (2013.01)

(58) Field of Classification Search
CPC ............ A61B 3/14; A61B 3/0008; A61B 3/12
USPC ............... 351/205, 206, 211, 214, 221
See application file for complete search history.

(56) References Cited

U.S. PATENT DOCUMENTS 5,061,049 A 10/1991 Hornbeck
5,663,781 A 9/1997 Wilms et al.
(Continued)

FOREIGN PATENT DOCUMENTS

CN 104665763 A 6/2015
EP 2878259 A1 6/2015
(Continued)

OTHER PUBLICATIONS

Office Action issued May 30, 2023 in Japanese Patent Application No. 2022-515754, 10 pages.
(Continued)

*Primary Examiner* — Mahidere S Sahle
(74) *Attorney, Agent, or Firm* — XSENSUS LLP

(57) ABSTRACT

An ophthalmological imaging device includes illumination optics having an illumination light source that outputs an illumination light, a scanner that redirects the illumination light toward a portion of an object to be imaged, and an optical image capture device including a camera that receives backscattered light that is scattered from the illumination light by the object and captures first and second images of the backscattered light. The device also includes a control processor that controls the scanner and the optical image capture device to cause the optical image capture device to capture the first and second images of the object. The first and second images are captured by the camera at different times and extracted from different portions of the backscattered light. The device also includes an image processor that generates a stereoscopic image from the first and second images of the object.

37 Claims, 30 Drawing Sheets

(56) References Cited

U.S. PATENT DOCUMENTS

| | | | |
|---|---|---|---|
| 6,758,564 | B2 | 7/2004 | Ferguson |
| 7,331,669 | B2 | 2/2008 | Elsner |
| 7,344,248 | B2 | 3/2008 | Zorn et al. |
| 7,831,106 | B2 | 11/2010 | Elsner et al. |
| 8,237,835 | B1 | 8/2012 | Muller |
| 8,488,895 | B2 | 7/2013 | Muller et al. |
| 2012/0165905 | A1 | 6/2012 | Liesfeld et al. |
| 2013/0222763 | A1 | 8/2013 | Bublitz et al. |
| 2014/0300864 | A1* | 10/2014 | Fukuma ............ A61B 3/102 351/206 |
| 2015/0150449 | A1 | 6/2015 | Matsumoto |
| 2018/0116502 | A1* | 5/2018 | Ishinabe ............ A61B 3/117 |
| 2020/0106929 | A1* | 4/2020 | Doyle ............ A61B 3/12 |

FOREIGN PATENT DOCUMENTS

| | | |
|---|---|---|
| JP | H03-500135 A | 1/1991 |
| JP | 2006-187312 A | 7/2006 |
| WO | 90/00024 A1 | 1/1990 |

OTHER PUBLICATIONS

International Search Report and Written Opinion mailed on Nov. 9, 2020, received for PCT Application PCT/JP2020/034225, Filed on Sep. 10, 2020, 10 pages.

Tyler, "Stereo Fundus Photography: Principles and Technique", Journal of Ophthalmic Photography, vol. 18, No. 2, Oct. 1996, pp. 68-81.

Muller et al., "Confocal Retinal Imaging Using a Digital Light Projector with a Near Infrared VCSEL Source", Proc SPIE Int Soc Opt Eng., Feb. 2018, pp. 1-16.

Espina et al., "Analysis of a Confocal Scanning Laser Ophthalmoscope Noncontact Ultra-Wide Field Lens System in Retinal and Choroidal Disease", Retina, vol. 35, No. 12, Dec. 2015, pp. 2664-2668.

Huang et al., "Optical Coherence Tomography". Science, Nov. 22, 1991, vol. 254, No. 5035, pp. 1178-1181.

Kim et al., "Real-Time Depth Reconstruction From Stereo Sequences" Proc. of SPIE, Three-Dimensional TV, Video, and Display IV, vol. 6016, No. 60160E, Nov. 15, 2005, pp. 60160E-1-60160E-12.

Gu et al., "Coded Rolling Shutter Photography: Flexible Space-Time Sampling", IEEE International Conference on Computational Photography (ICCP), Mar. 2010, pp. 1-8.

Kafieh et al., "A Review of Algorithms For Segmentation of Optical Coherence Tomography From Retina", Journal of Medical Signals & Sensors, vol. 3, Issue 1, Jan.-Mar. 2013, pp. 45-60.

Chen, Spectral Domain Optical Coherence Tomography in Glaucoma: Qualitative and Quantitative Analysis of the Optic Nerve Head and Retinal Nerve Fiber Layer (an AOS thesis). Trans Am Ophthalmol Soc., vol. 107, 2009, pp. 254-281.

Chinese Office Action issued Feb. 26, 2025, in corresponding Chinese Patent Application No. 202080064030.2, 14pp.

* cited by examiner

[Fig. 1]
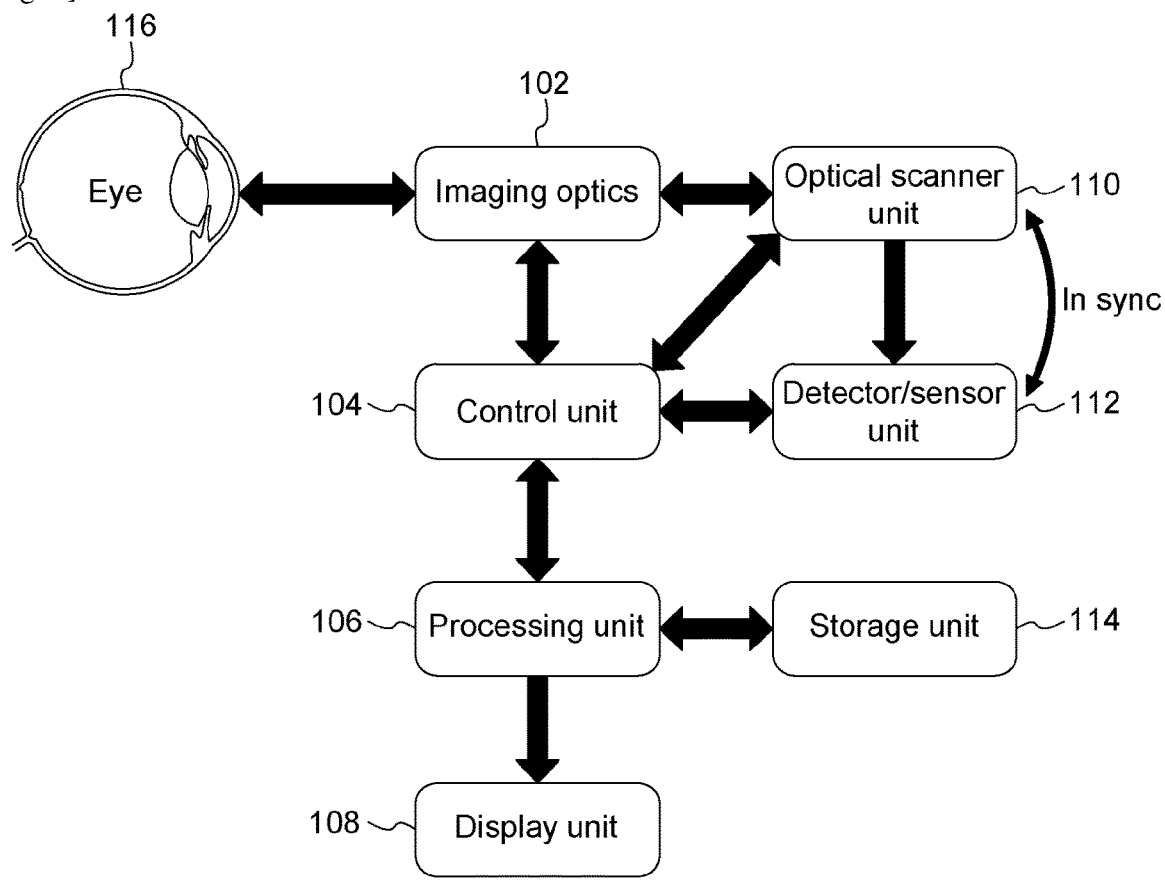
[Fig. 2A]
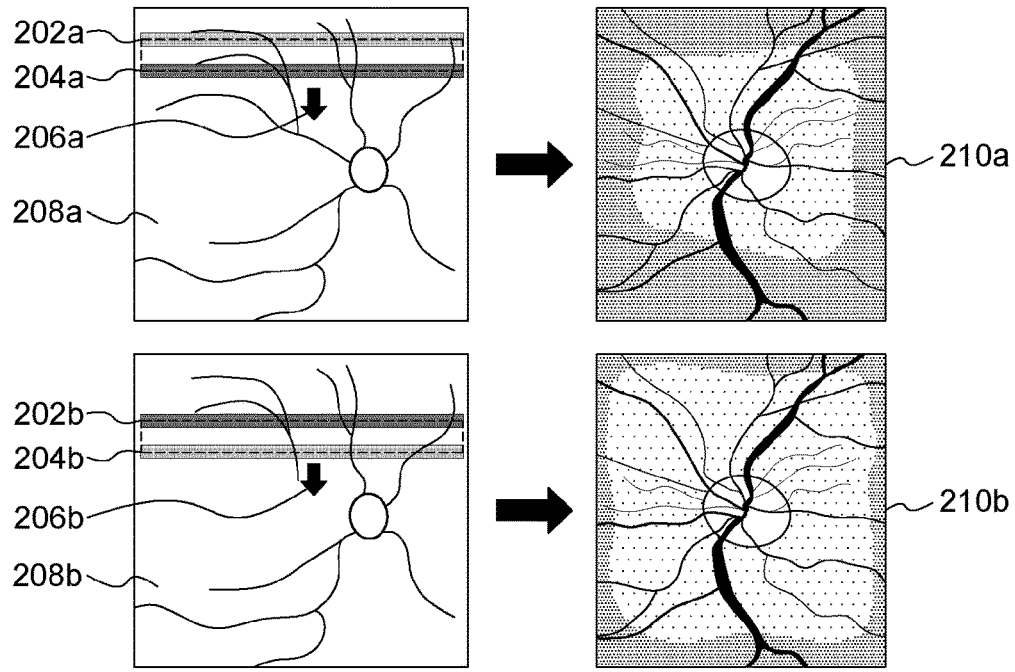

[Fig. 2B]
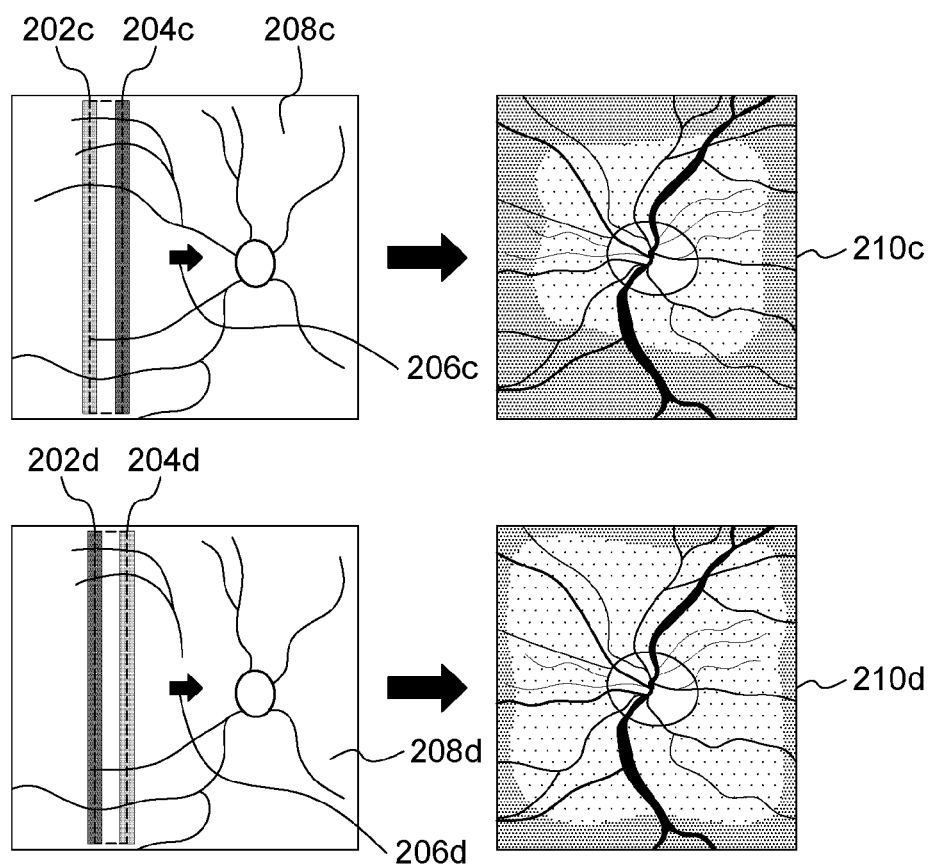

[Fig. 2C]
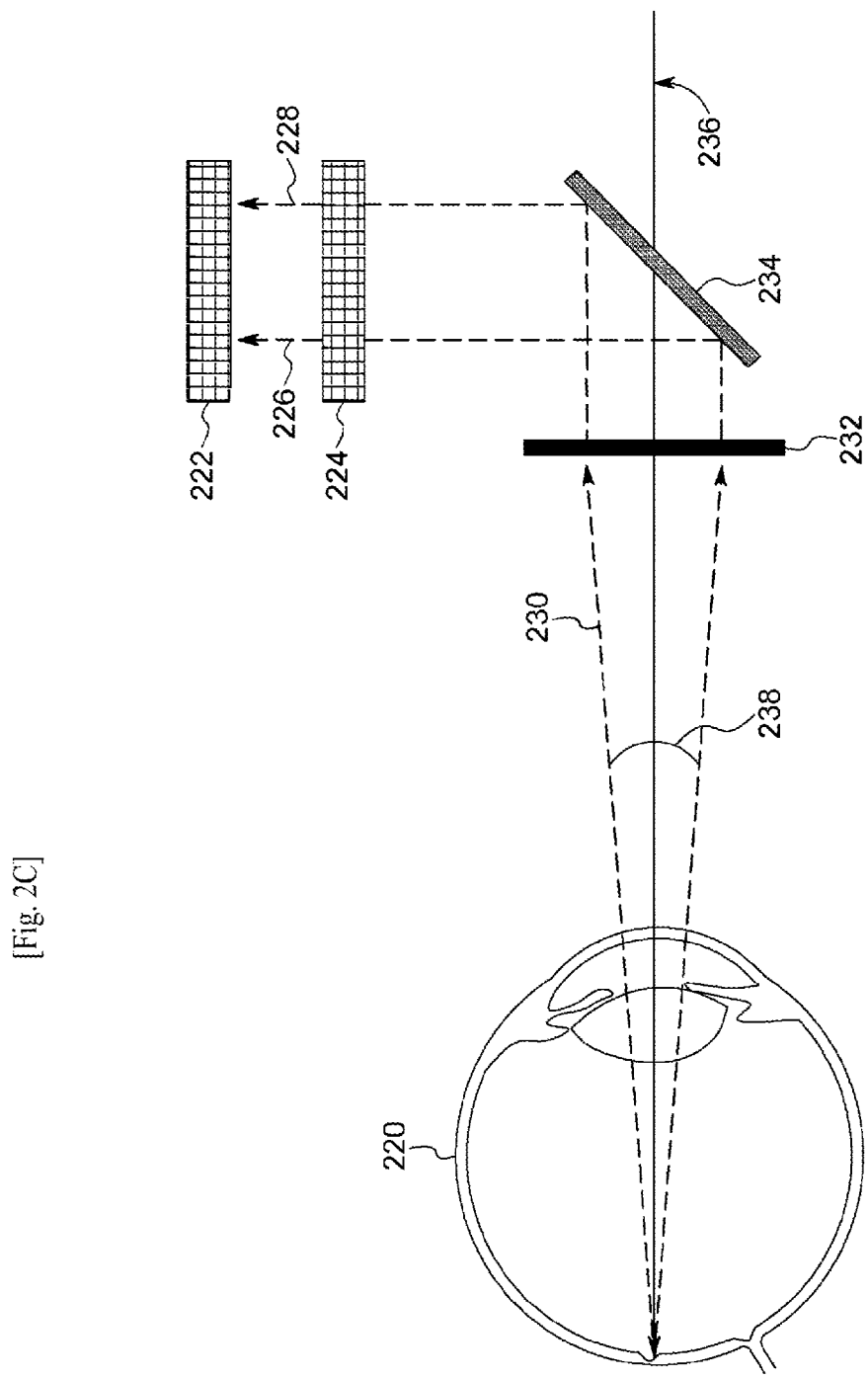

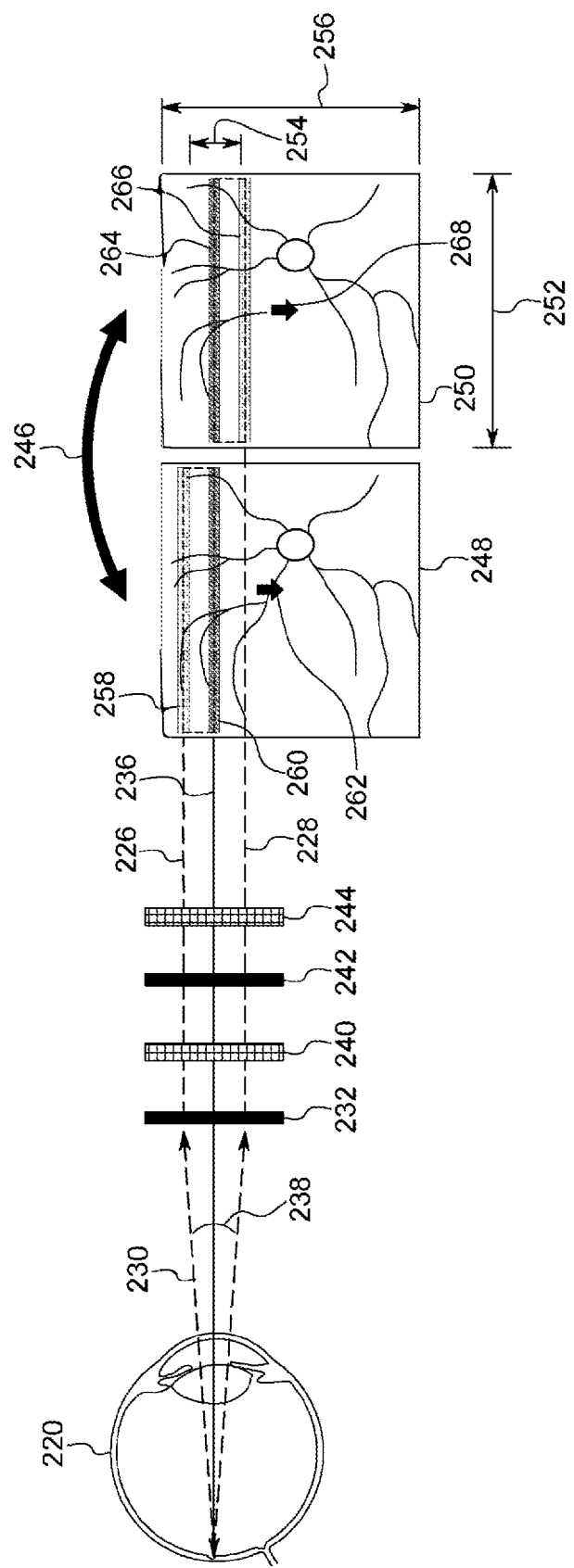
[Fig. 2D]

[Fig. 2E]
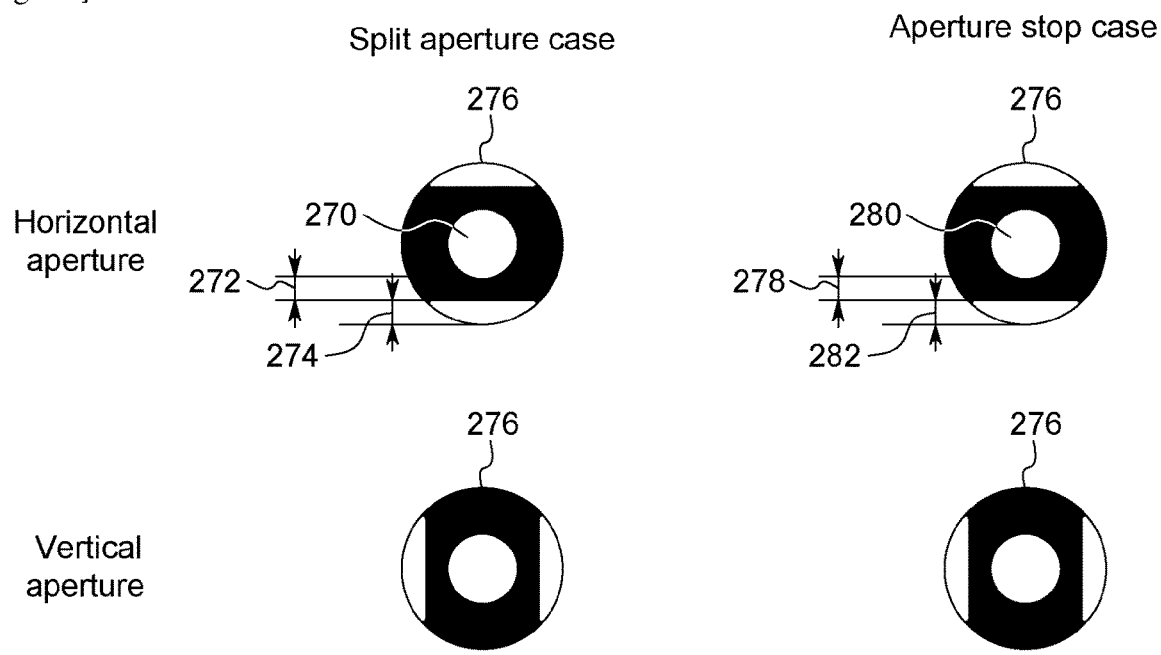

[Fig. 2F]
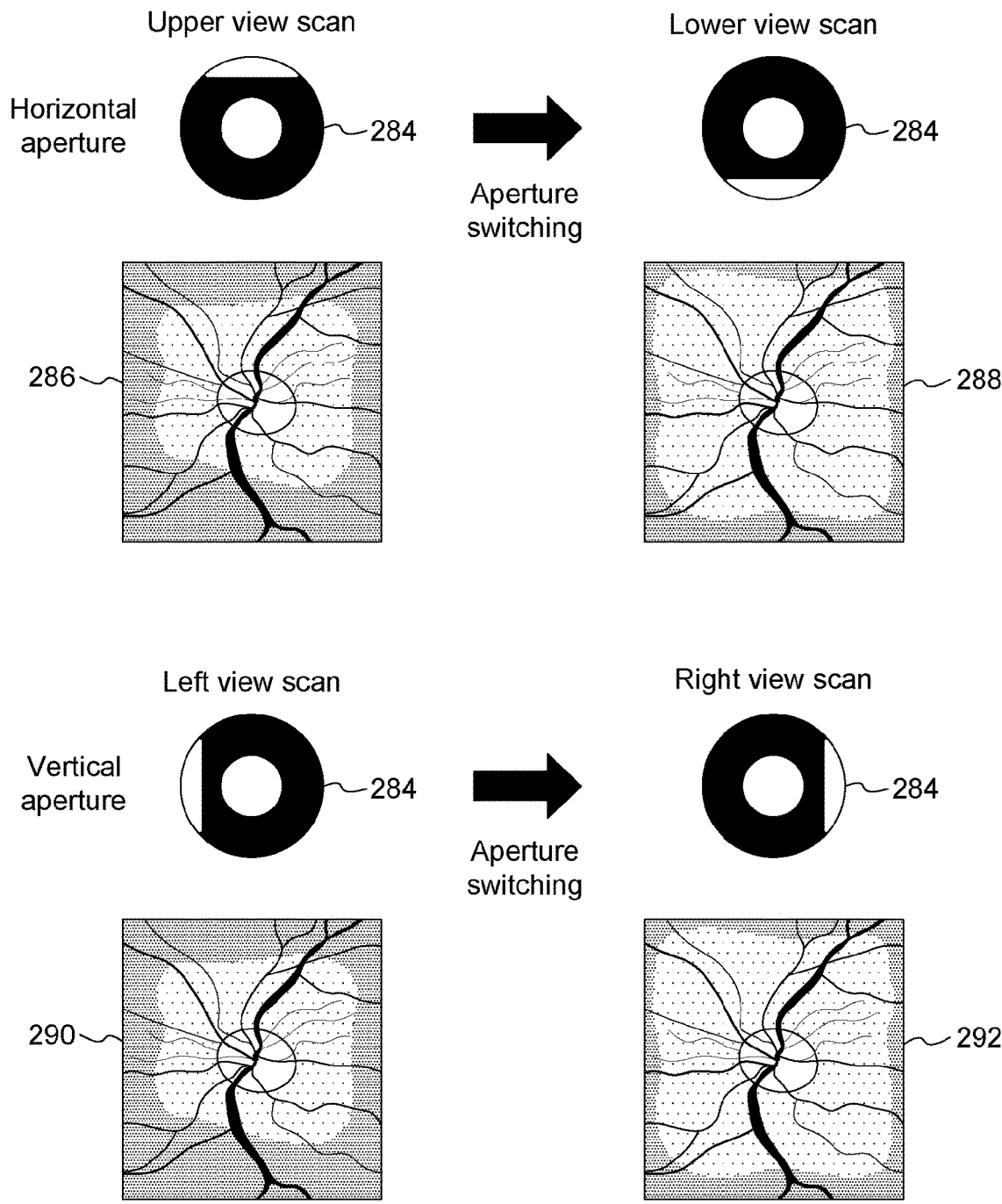

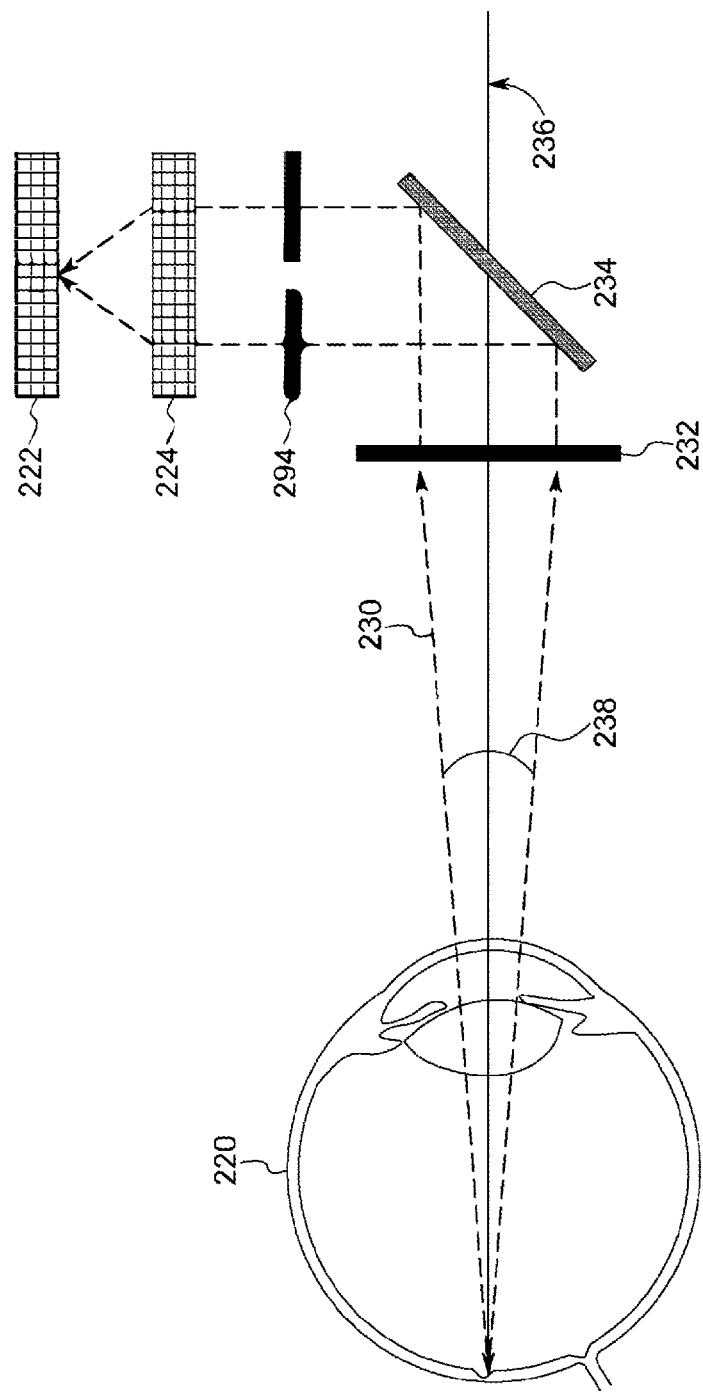
[Fig. 2G]

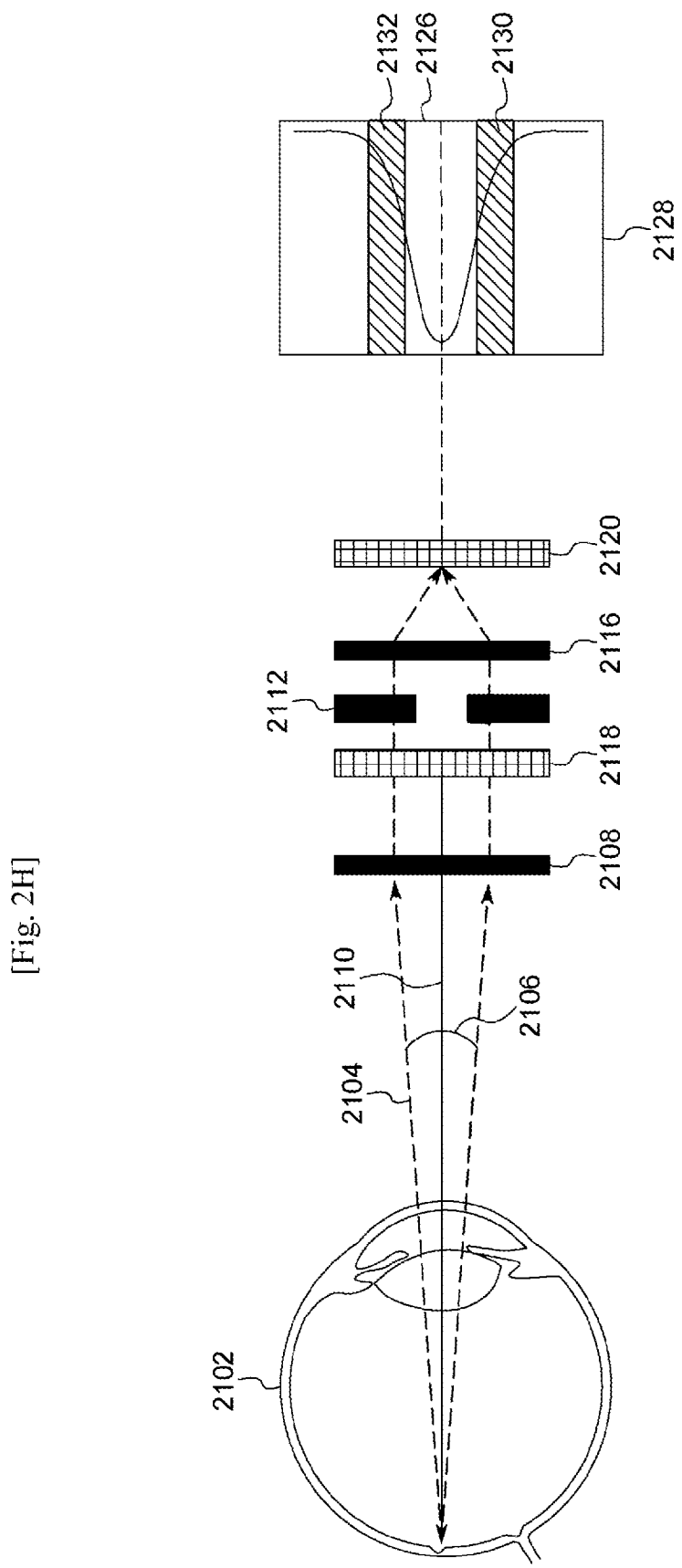
[Fig. 2H]

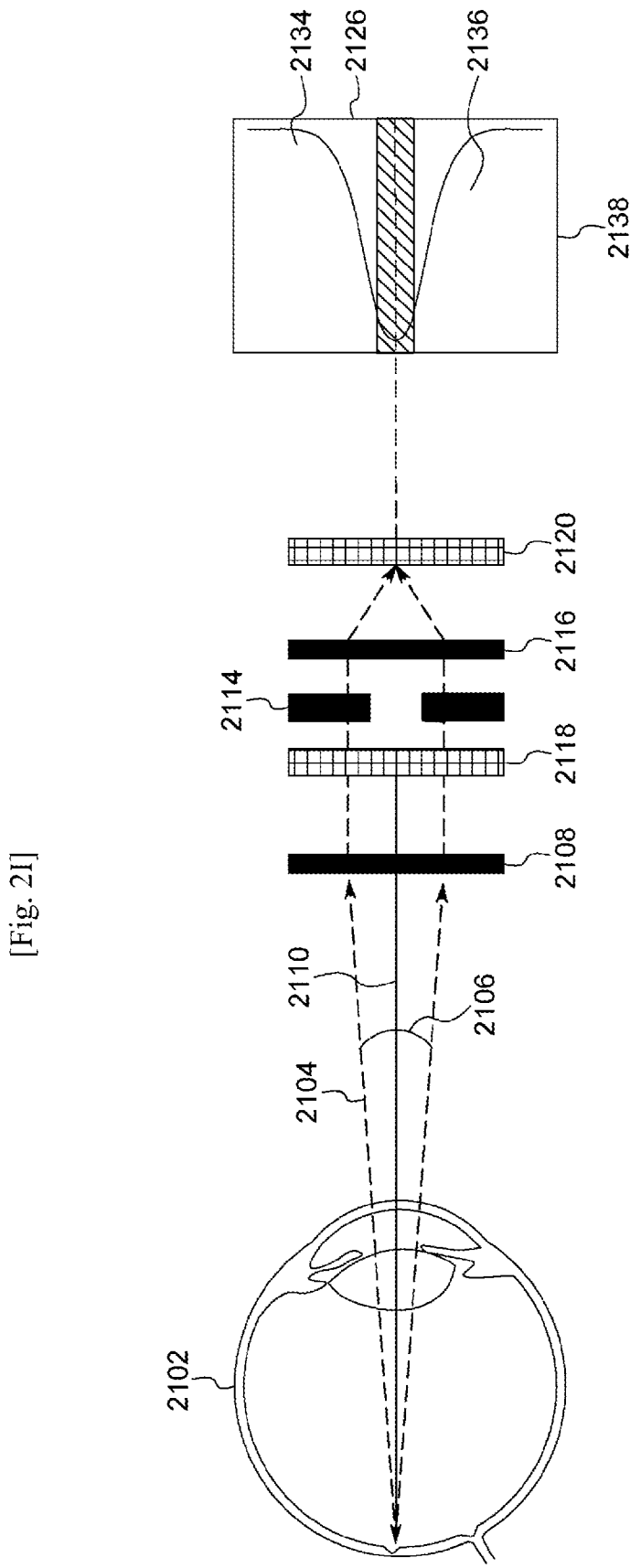

[Fig. 2J]
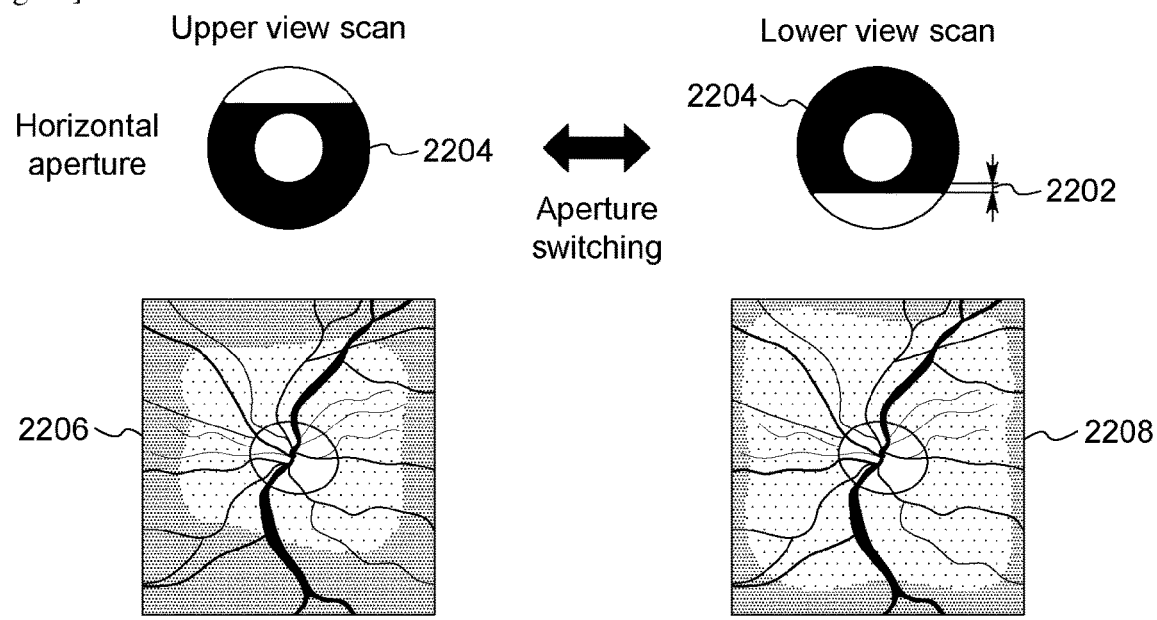
[Fig. 2K]
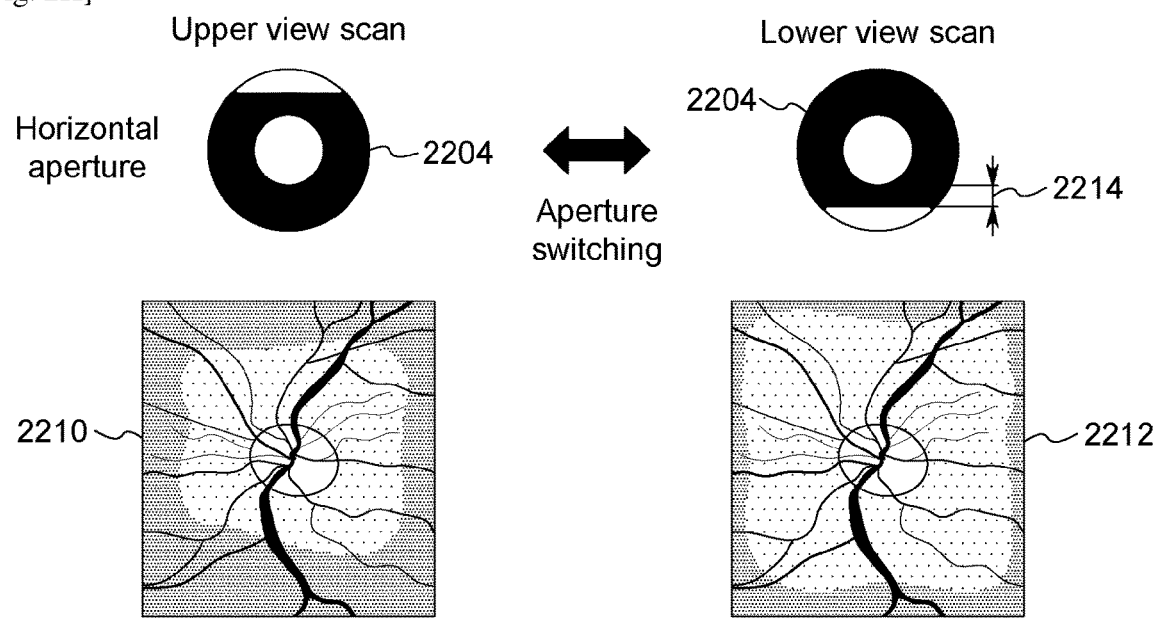

[Fig. 3A]
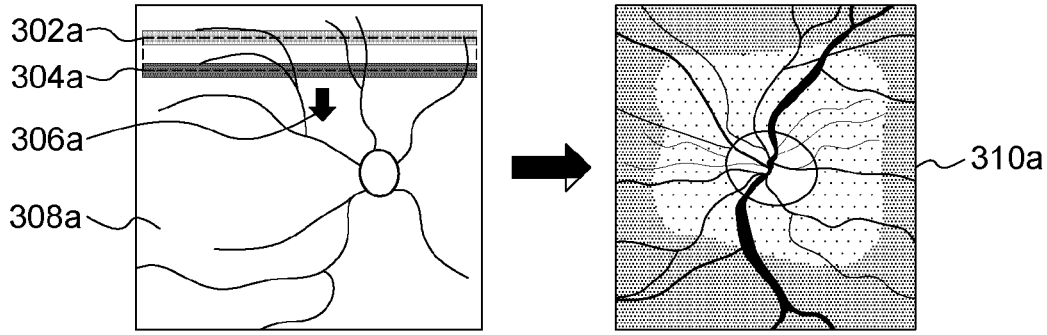
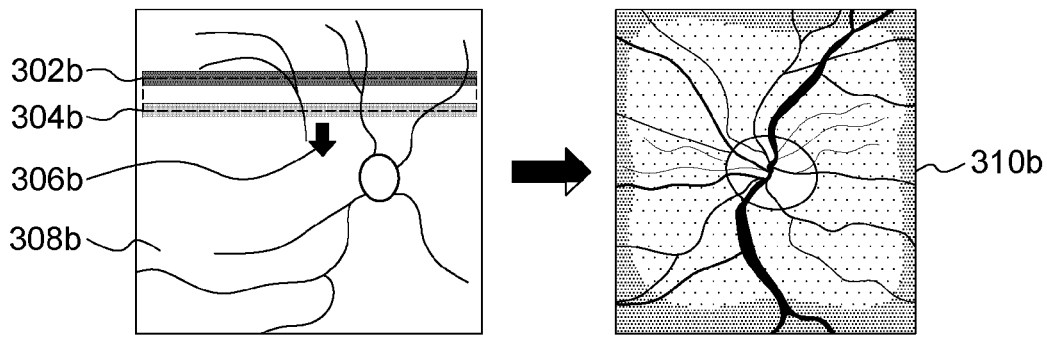
[Fig. 3B]
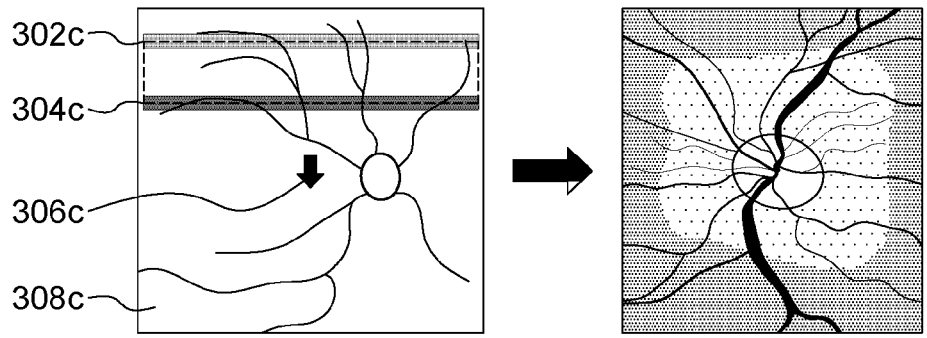
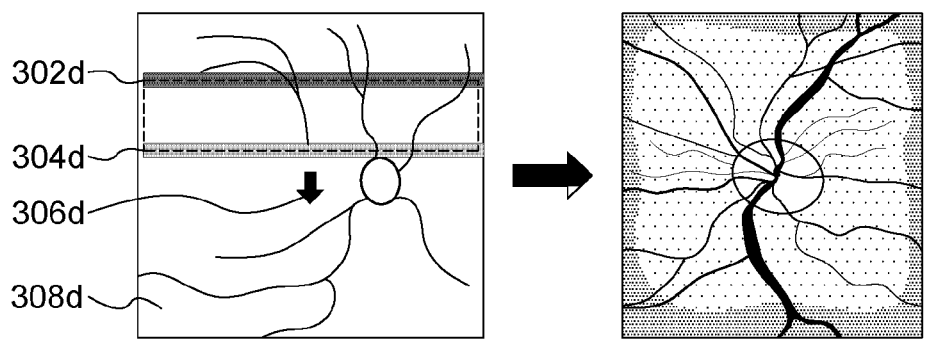

[Fig. 4A]
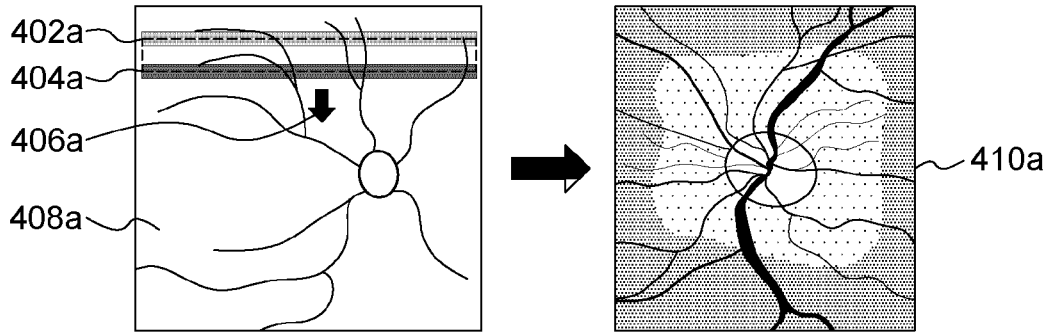
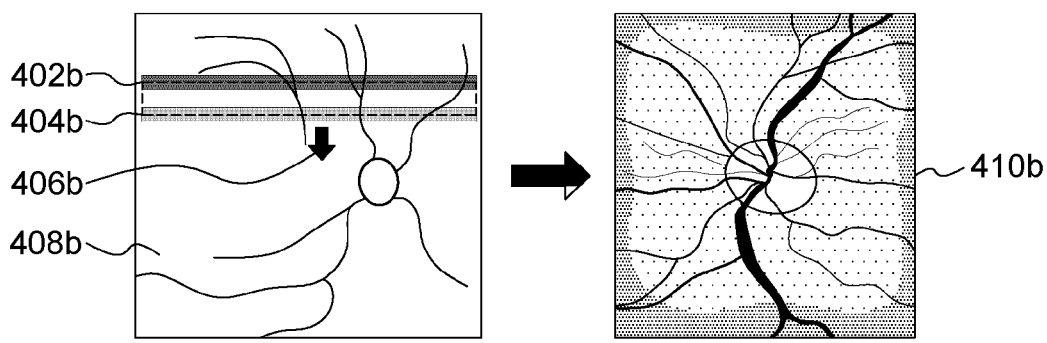
[Fig. 4B]
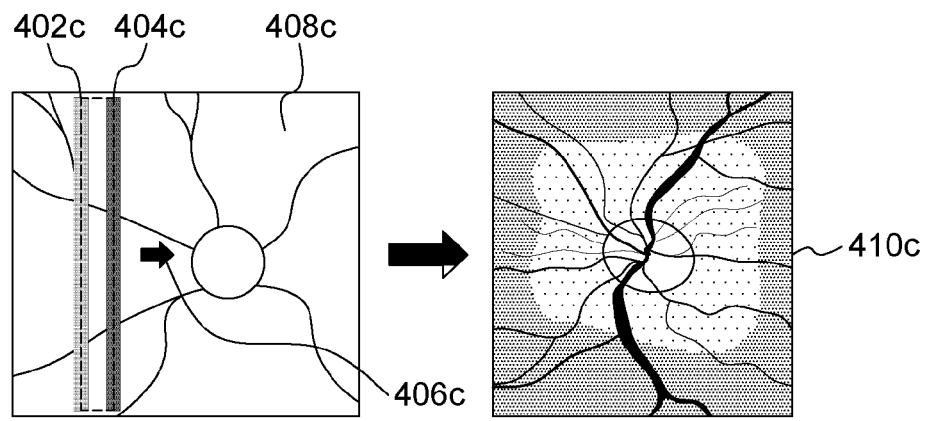
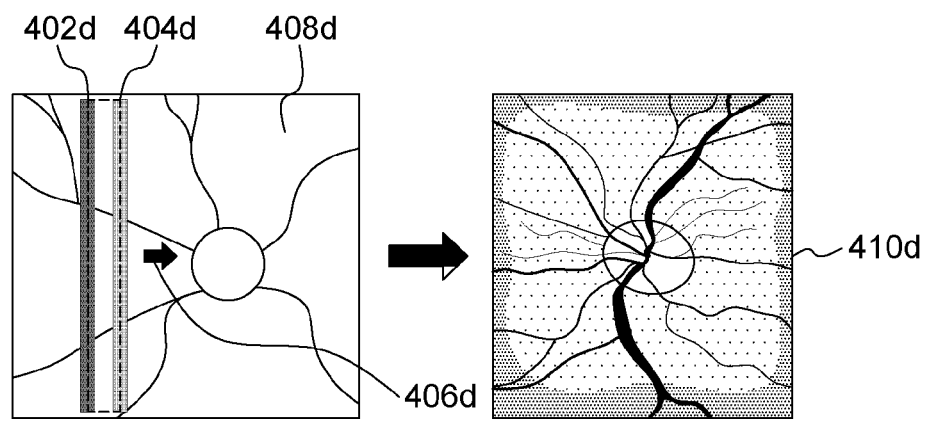

[Fig. 4C]
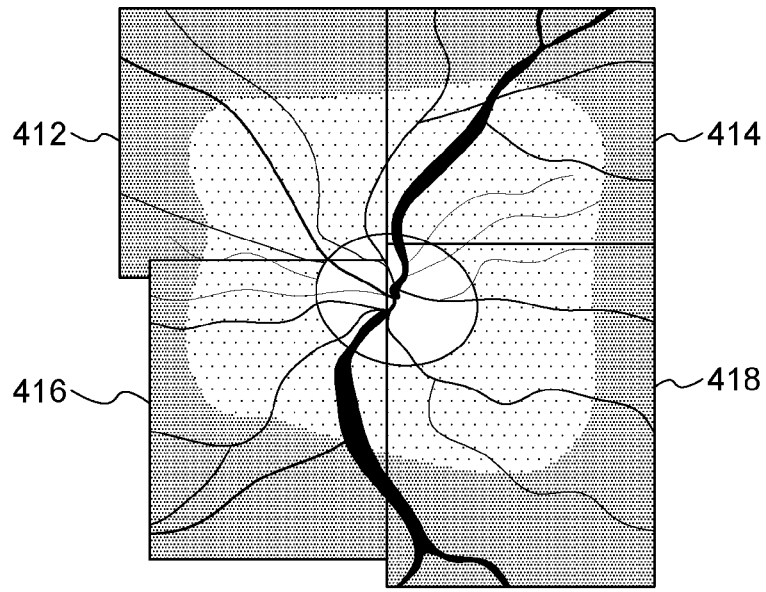
[Fig. 4D]
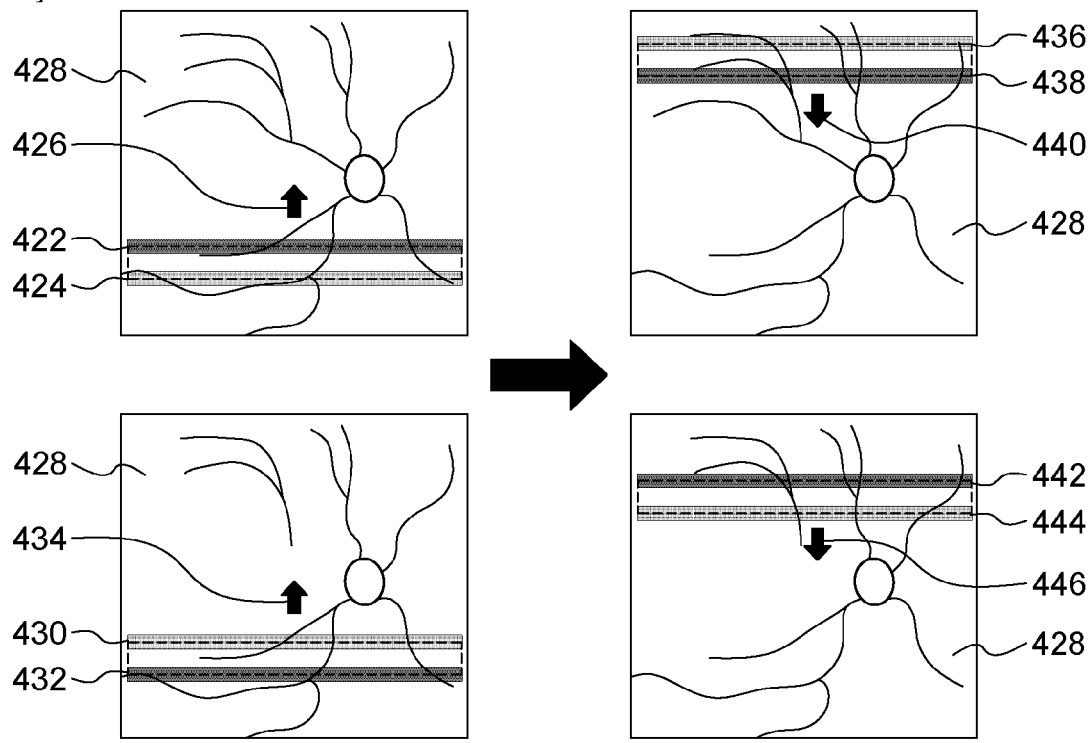

[Fig. 5]
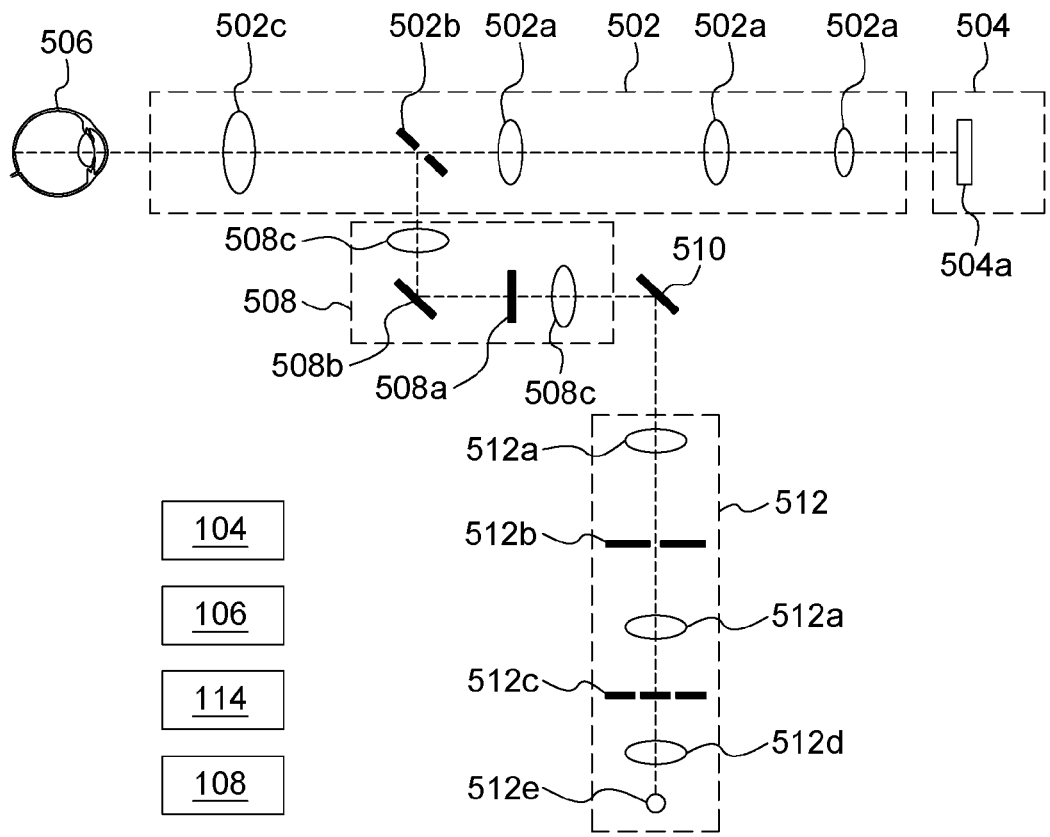
[Fig. 6A]
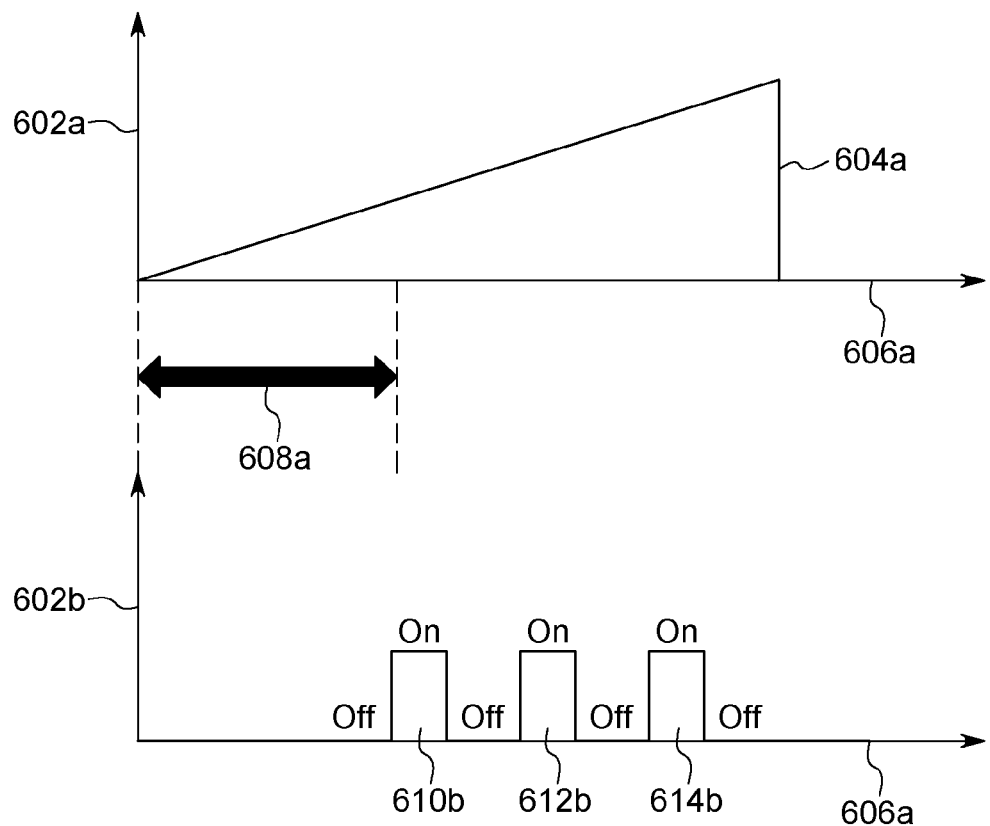

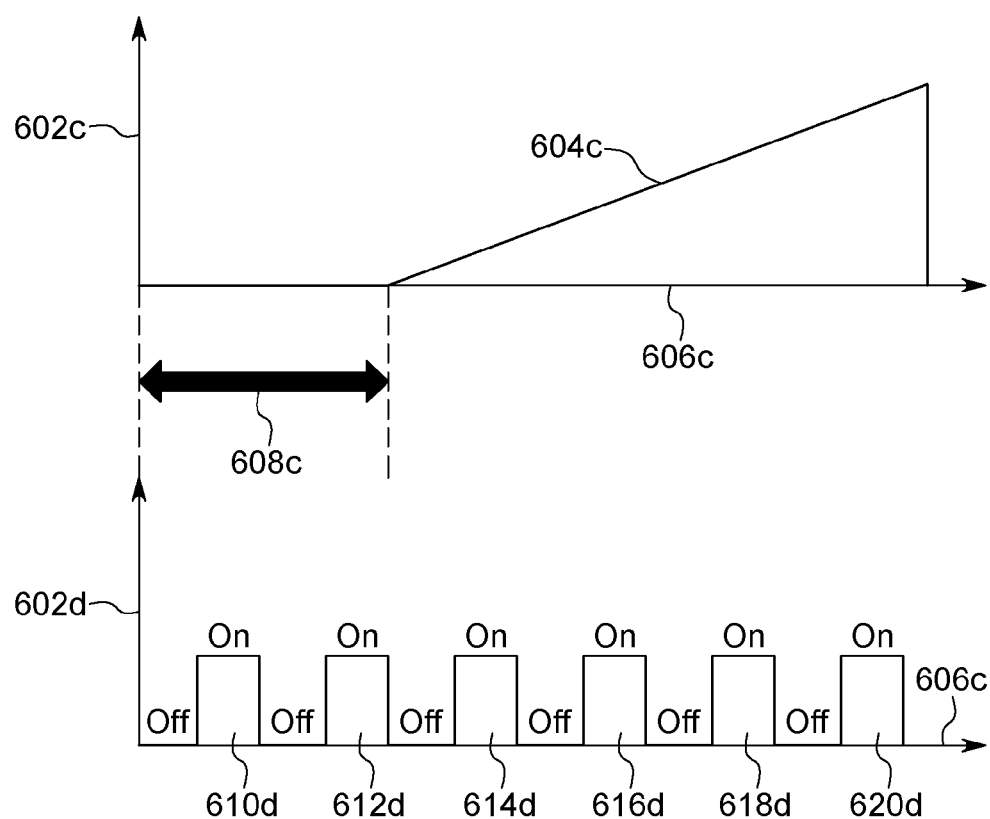
[Fig. 6B]

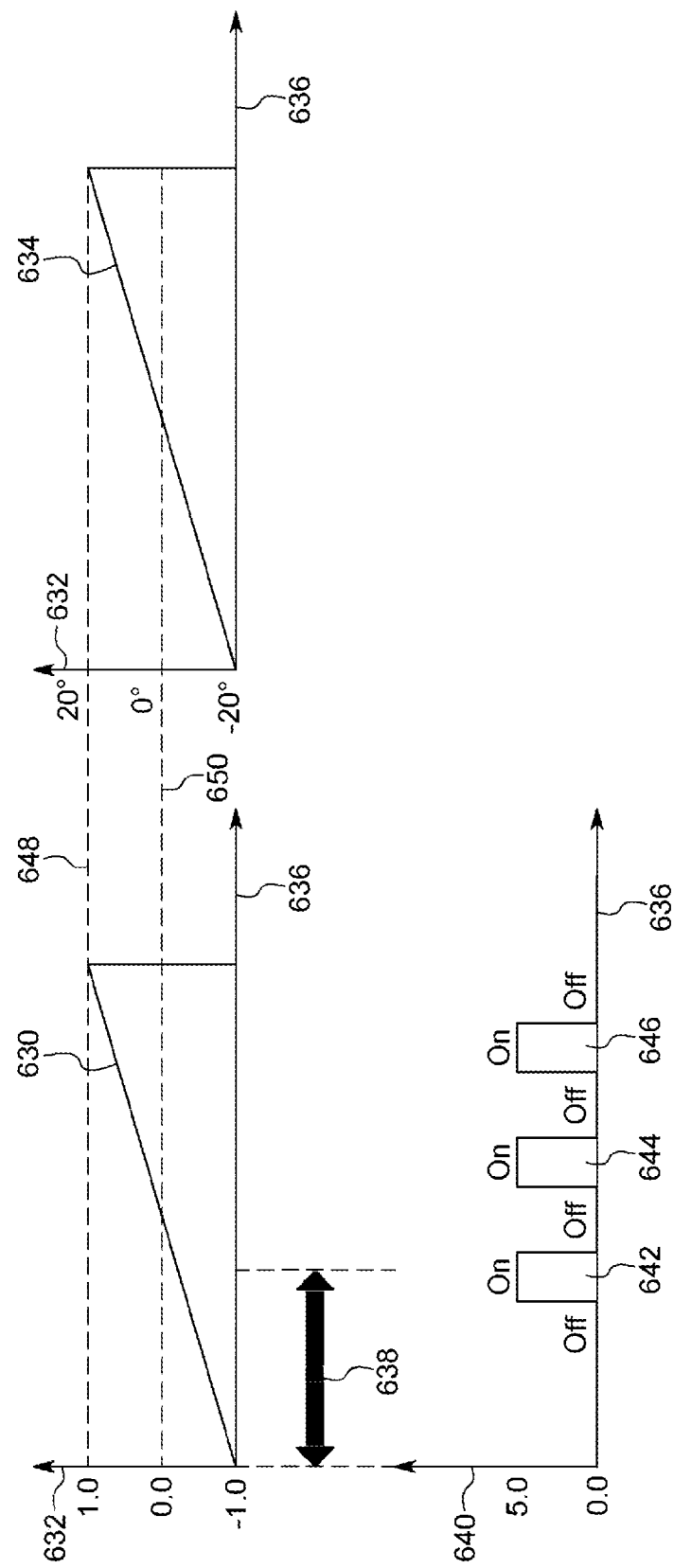
[Fig. 6C]

[Fig. 7A]
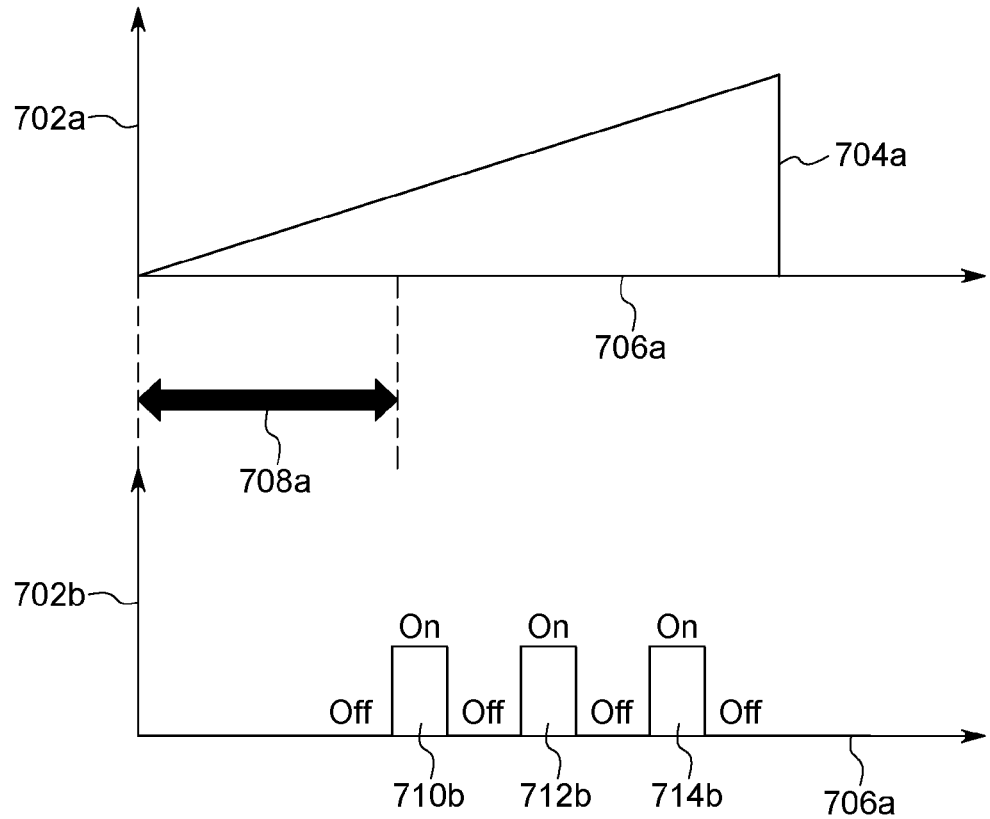
[Fig. 7B]
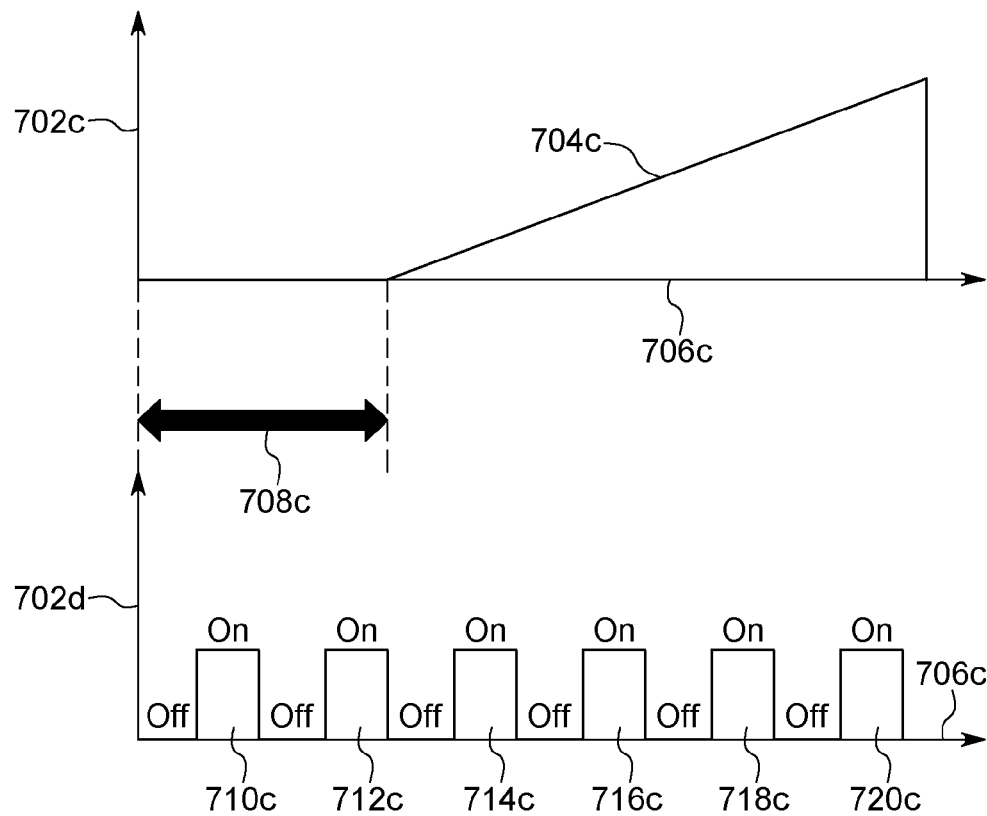

[Fig. 7C]
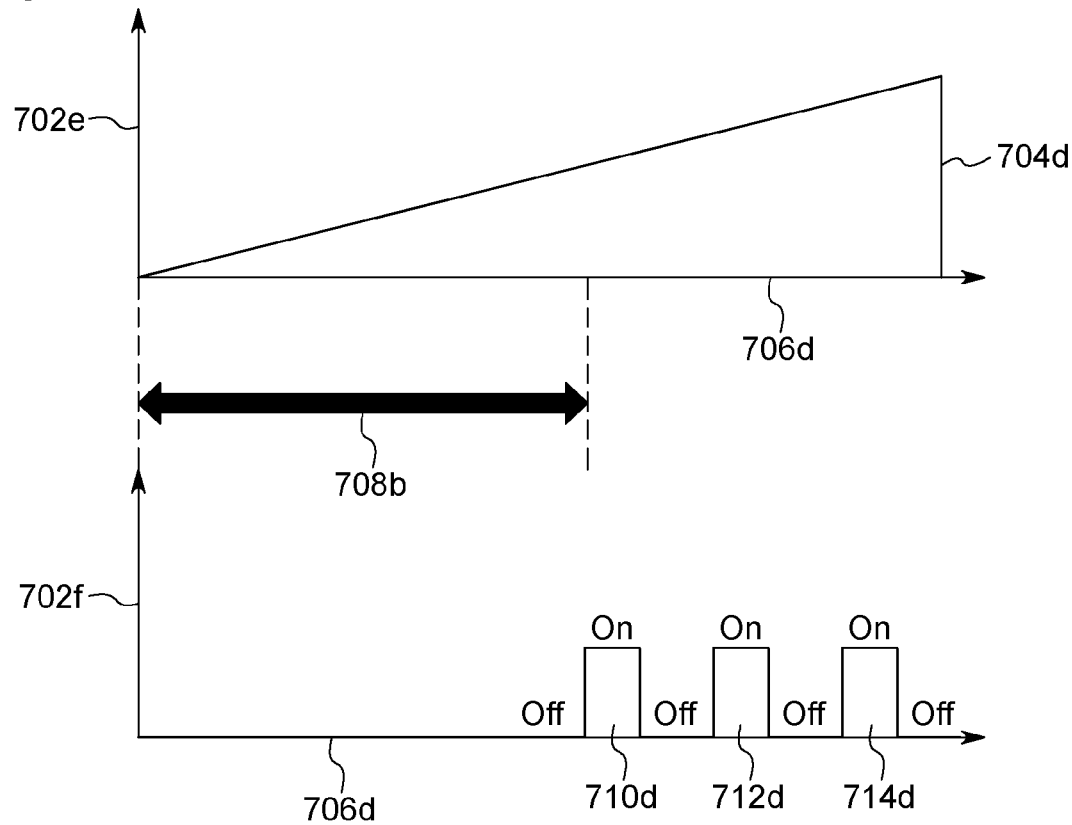
[Fig. 7D]
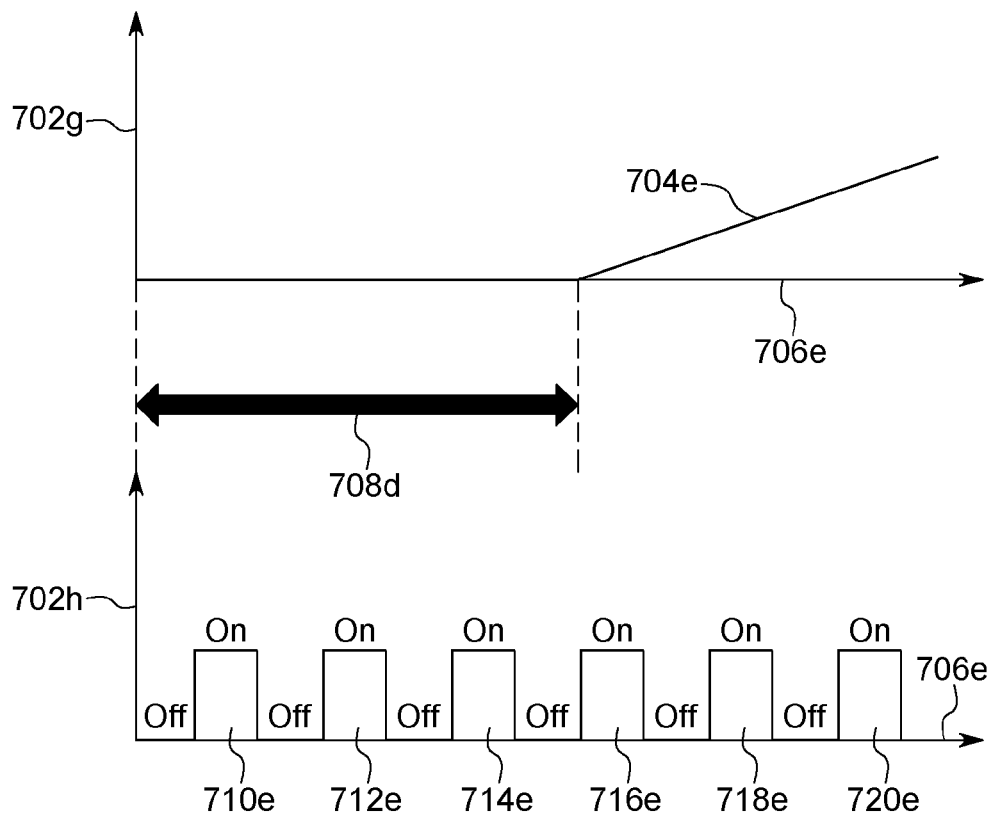

[Fig. 8]
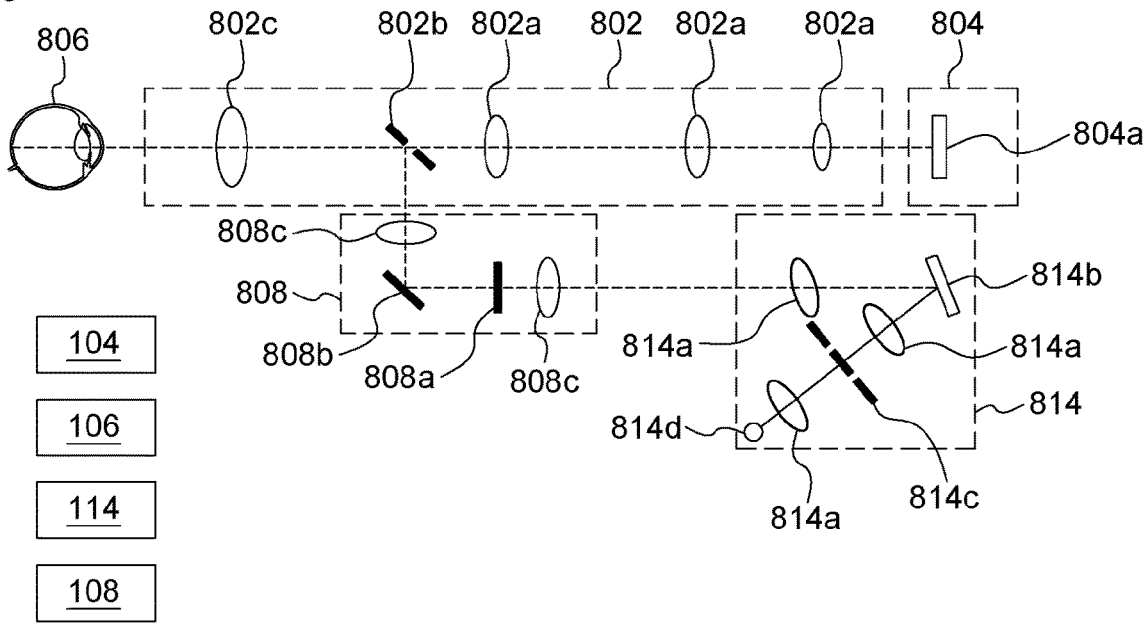
[Fig. 9A]
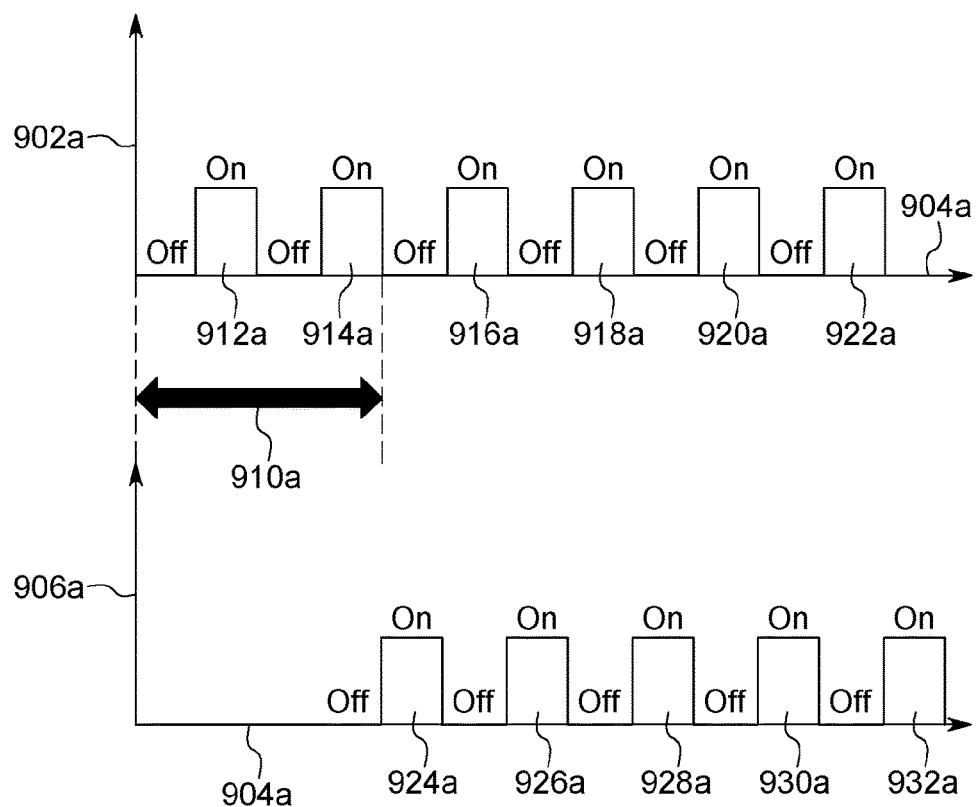

[Fig. 9B]
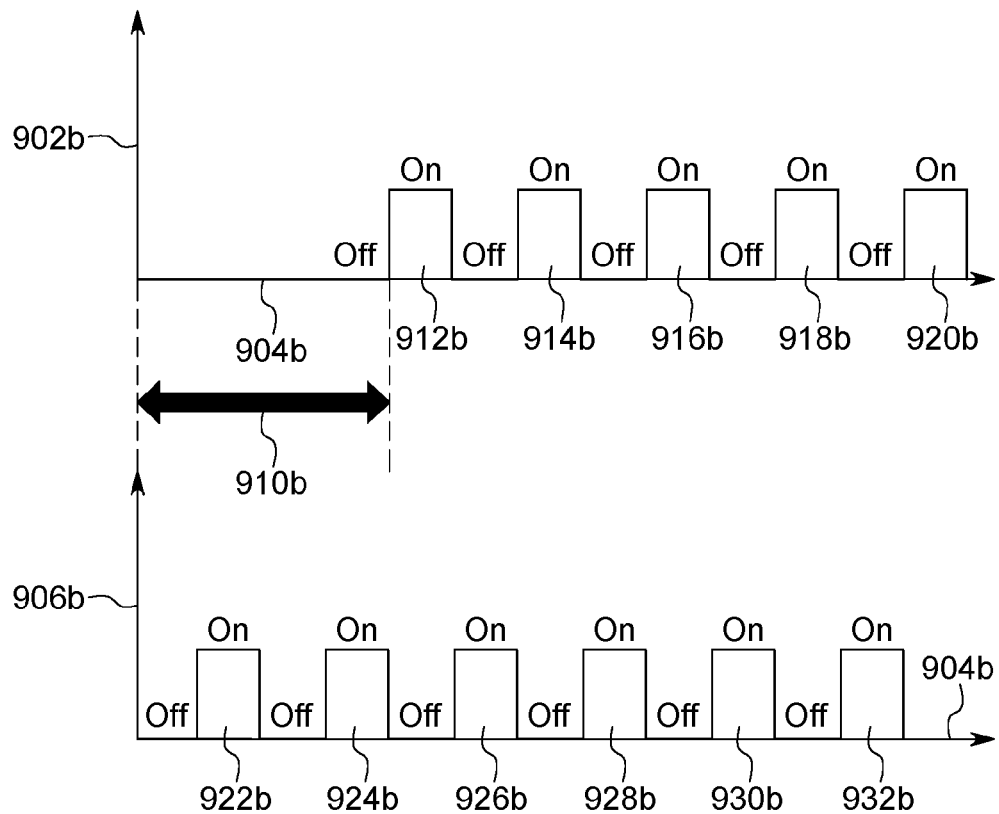
[Fig. 10A]
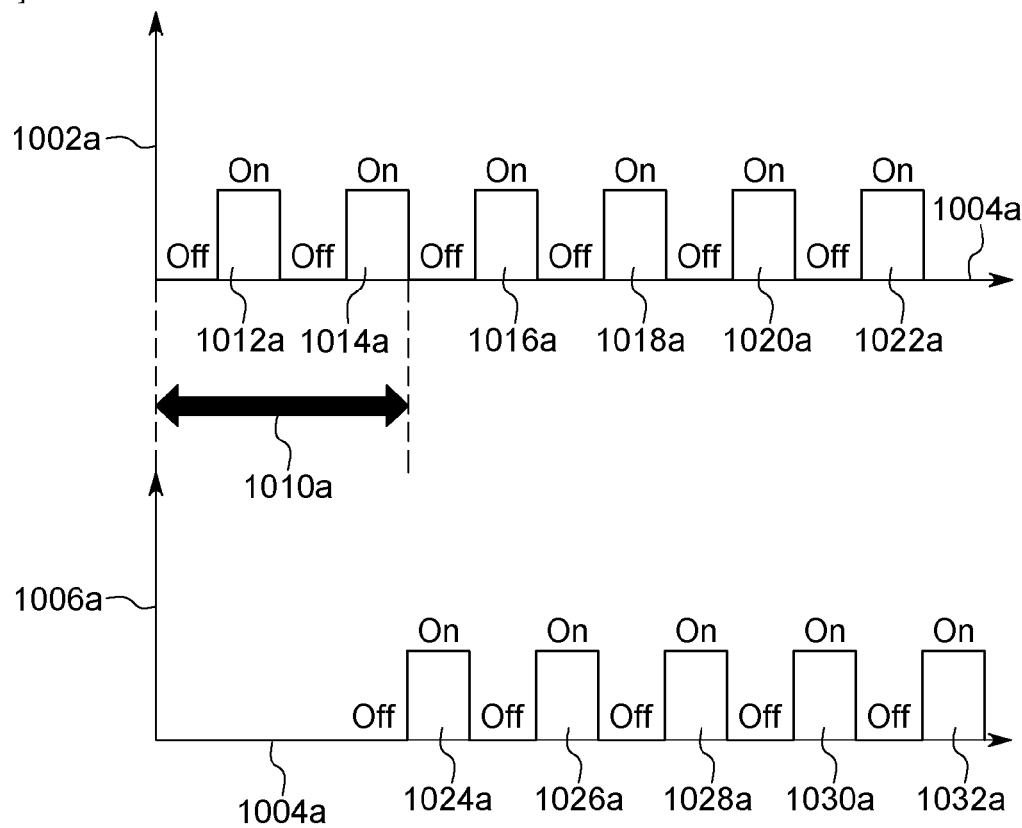

[Fig. 10B]
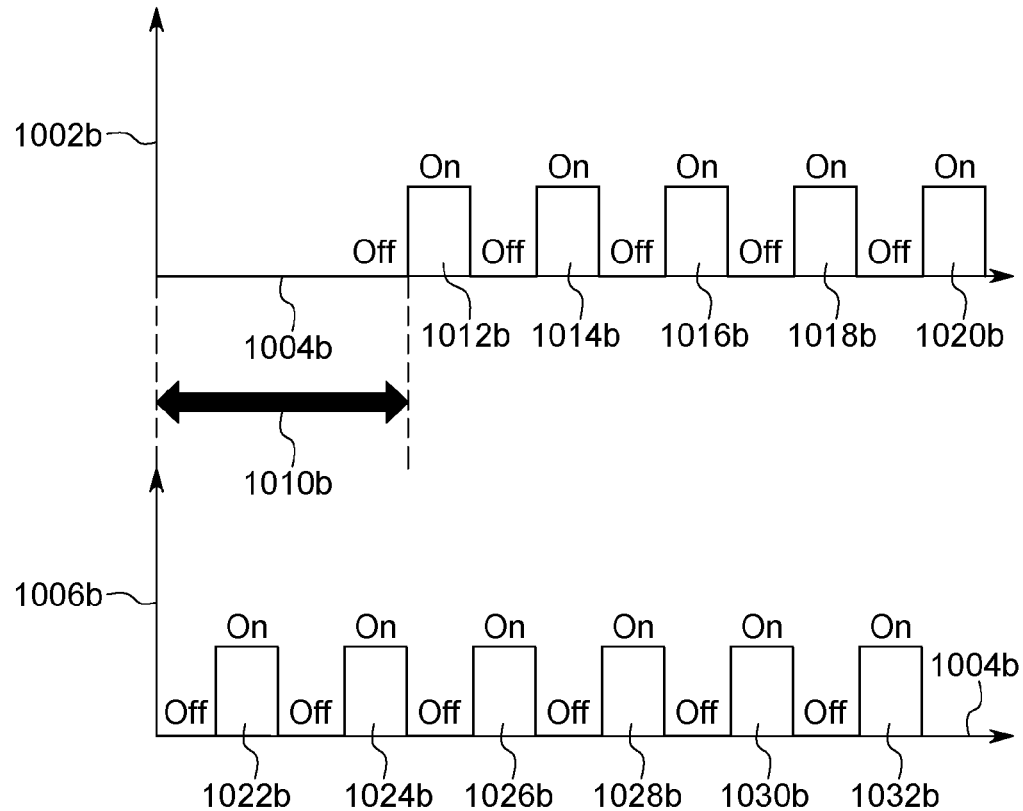
[Fig. 10C]
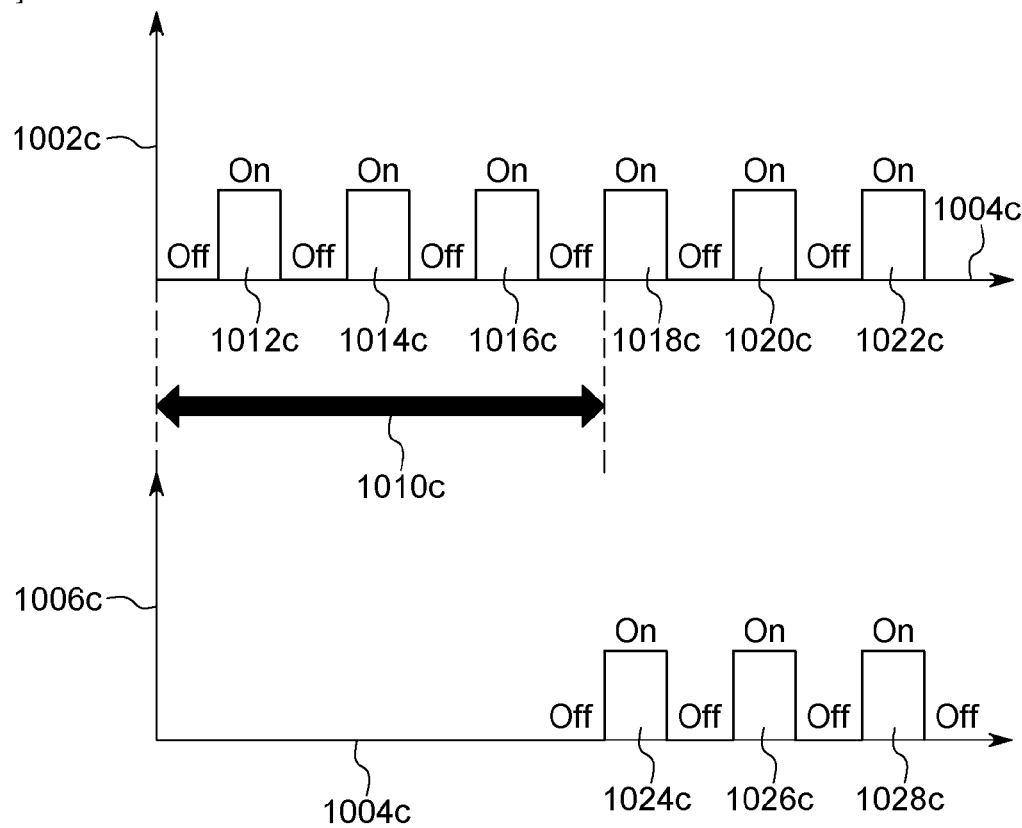

[Fig. 10D]
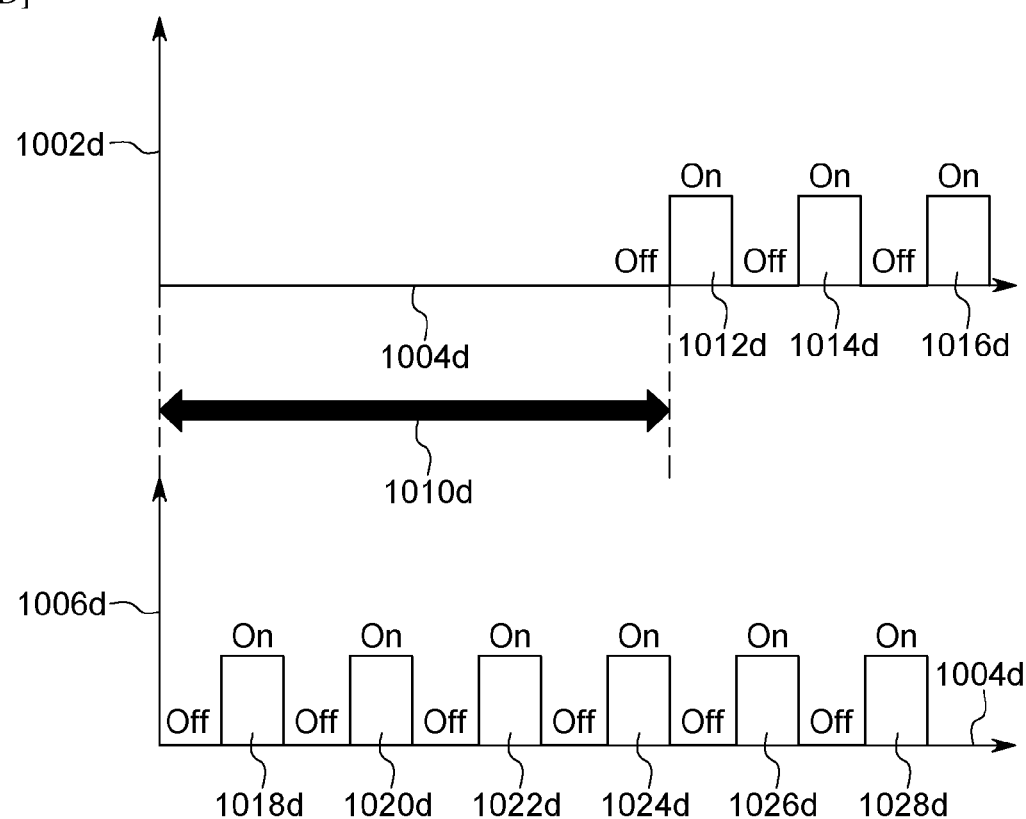

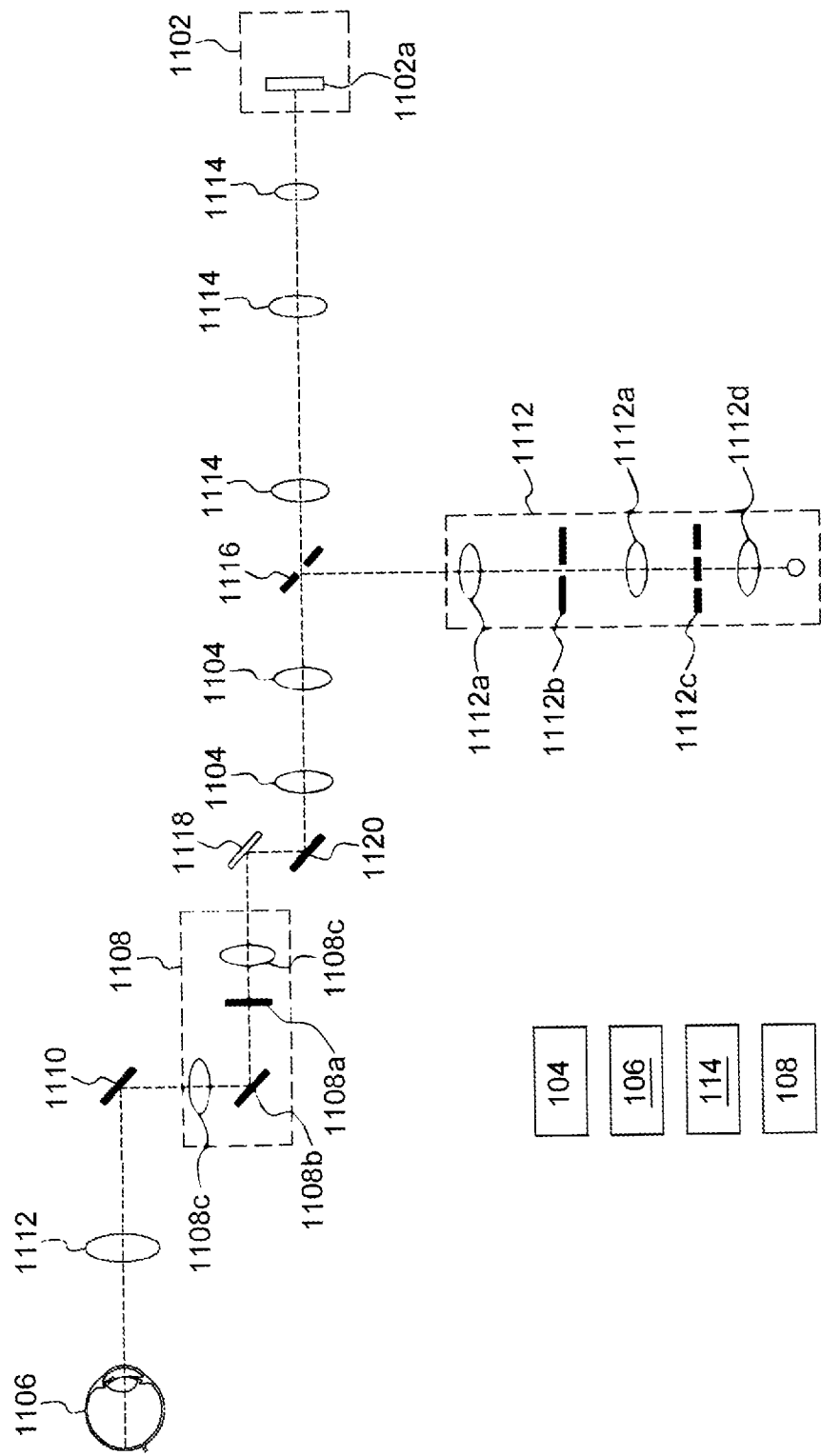
[Fig. 11A]

[Fig. 11B]
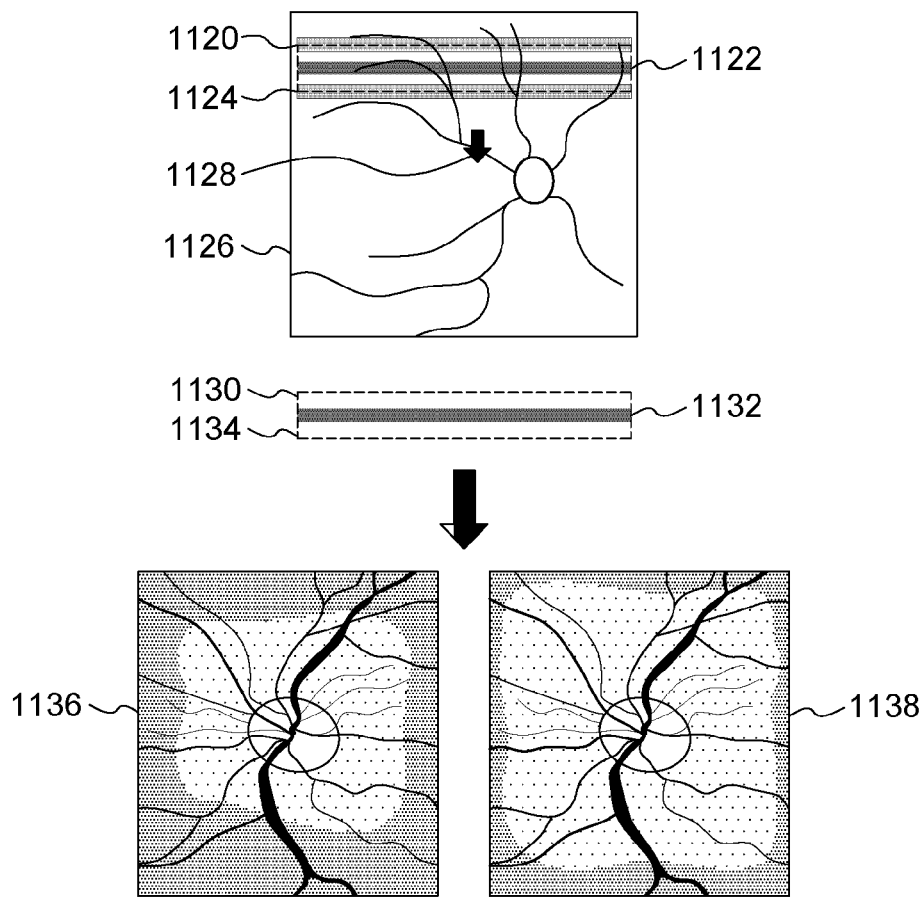
[Fig. 12A]
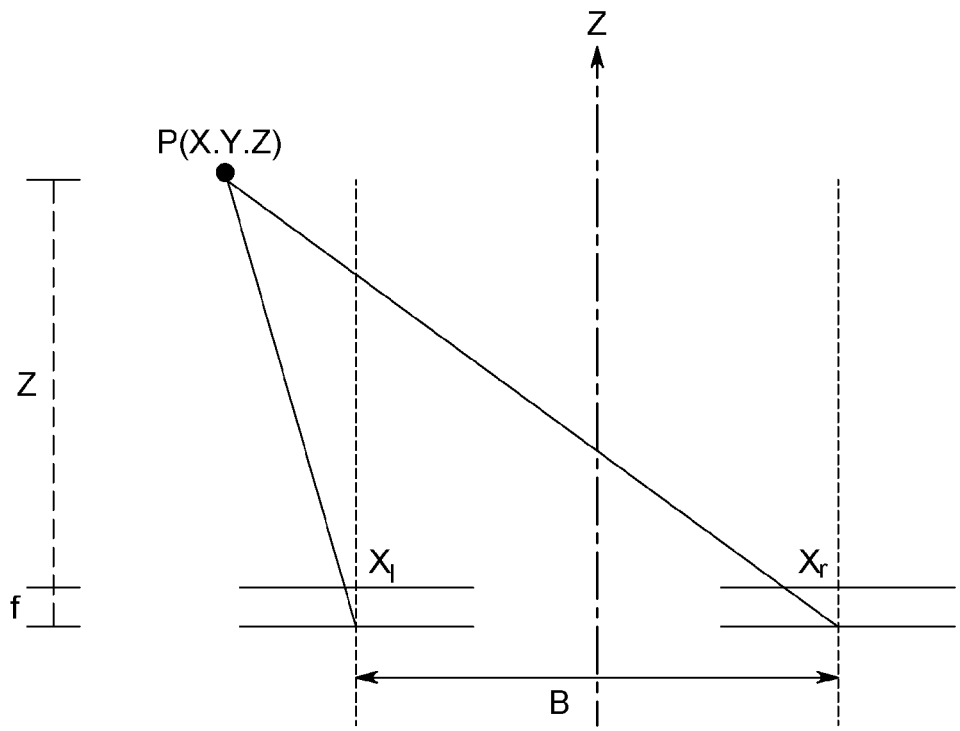

[Fig. 12B]
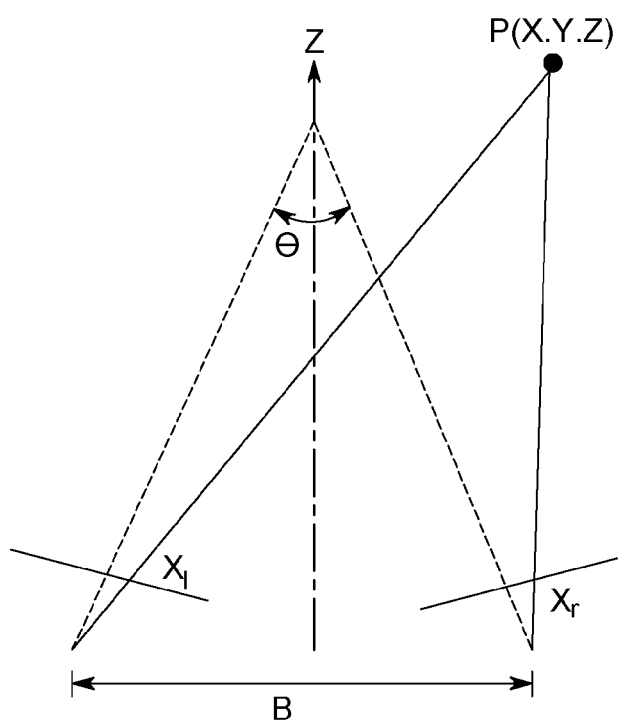

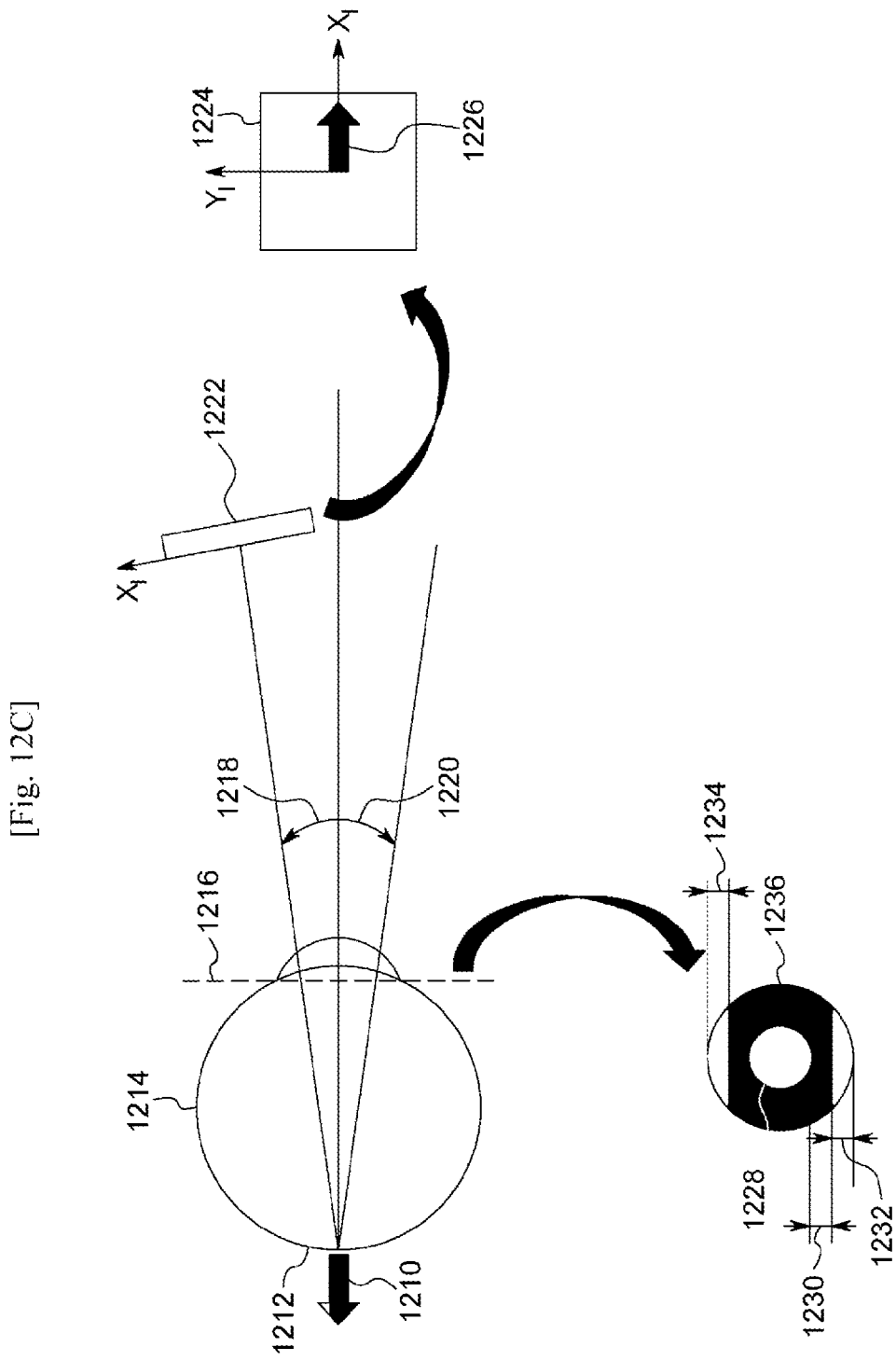
[Fig. 12C]

[Fig. 13]
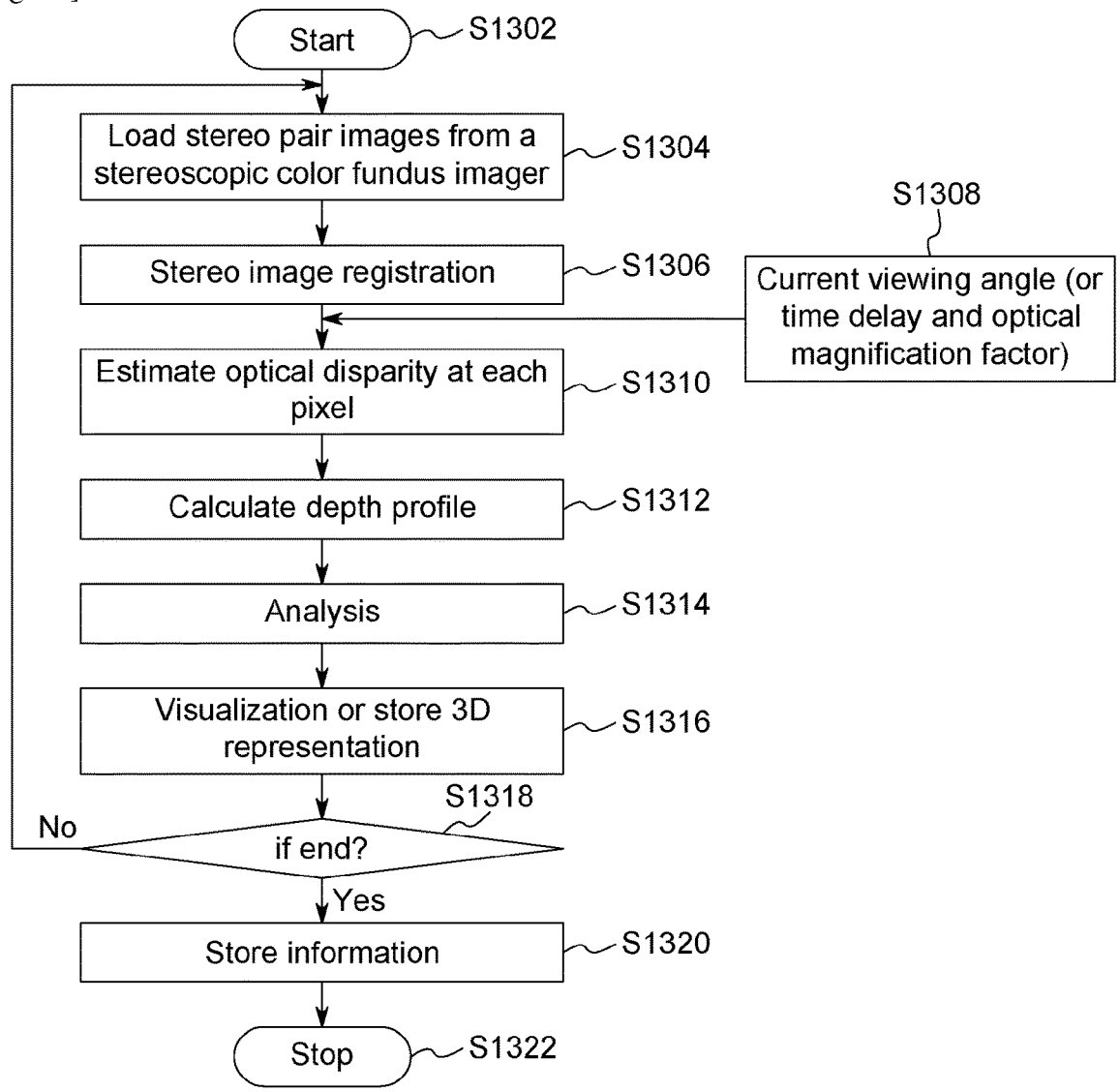
[Fig. 14A]
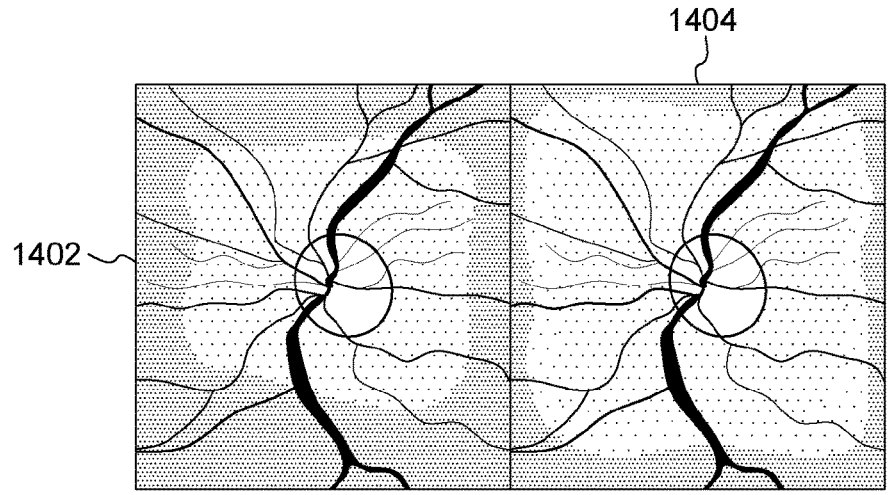

[Fig. 14B]
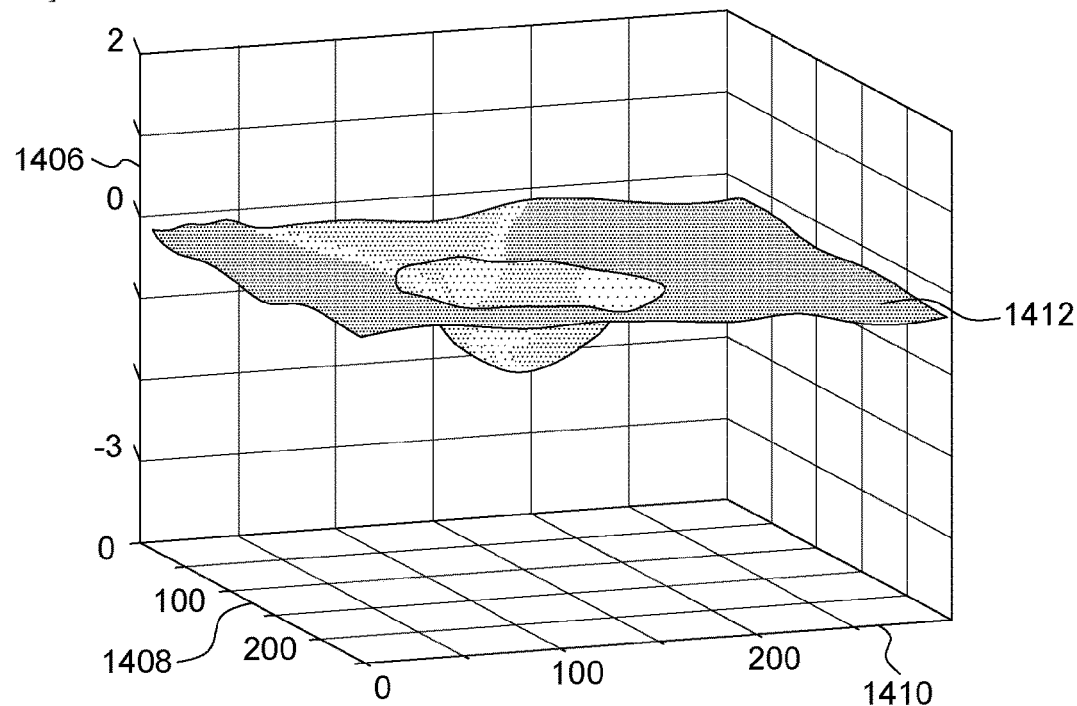
[Fig. 15A]
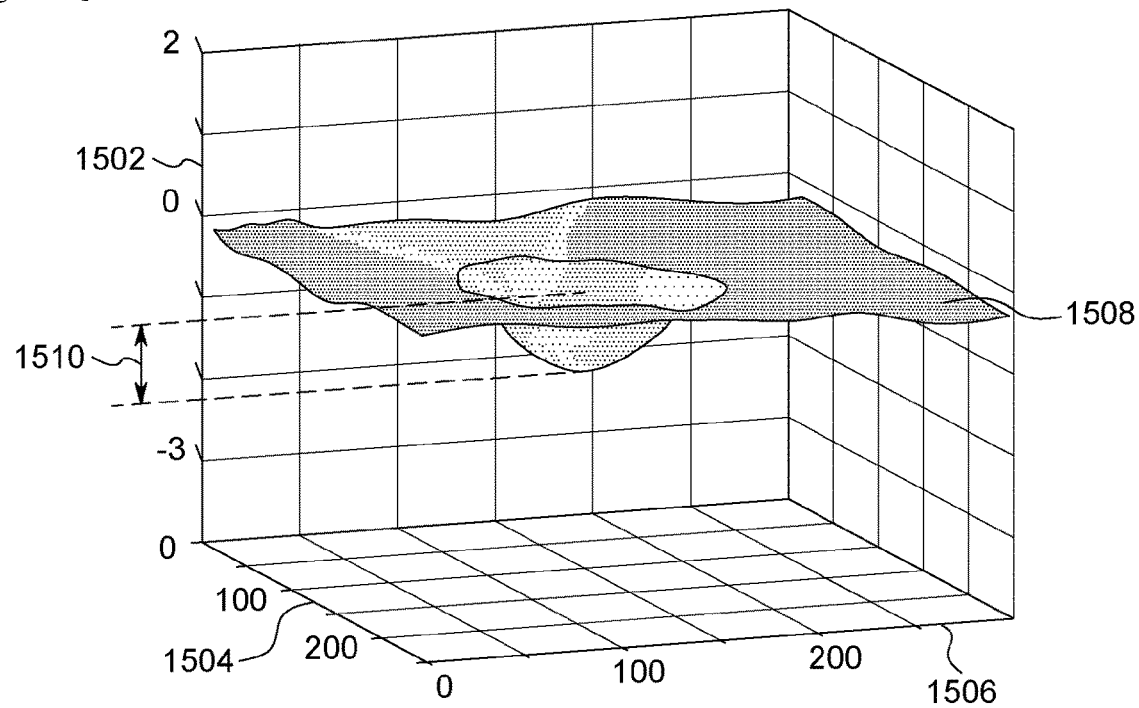

[Fig. 15B]
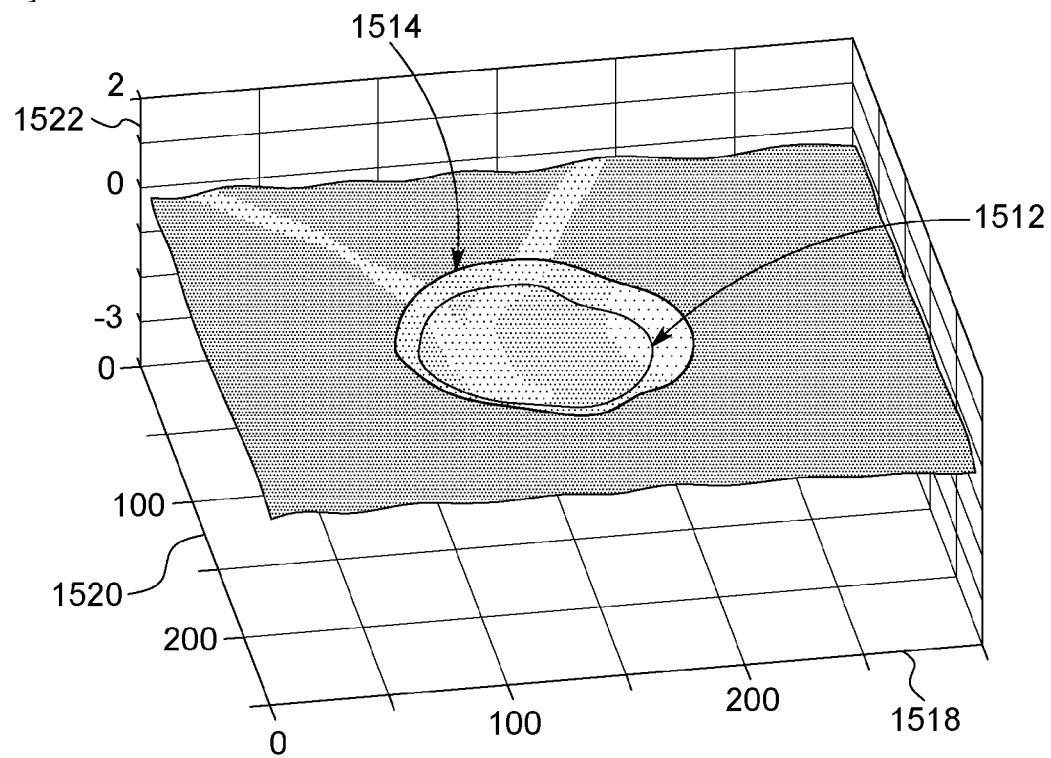

[Fig. 16]
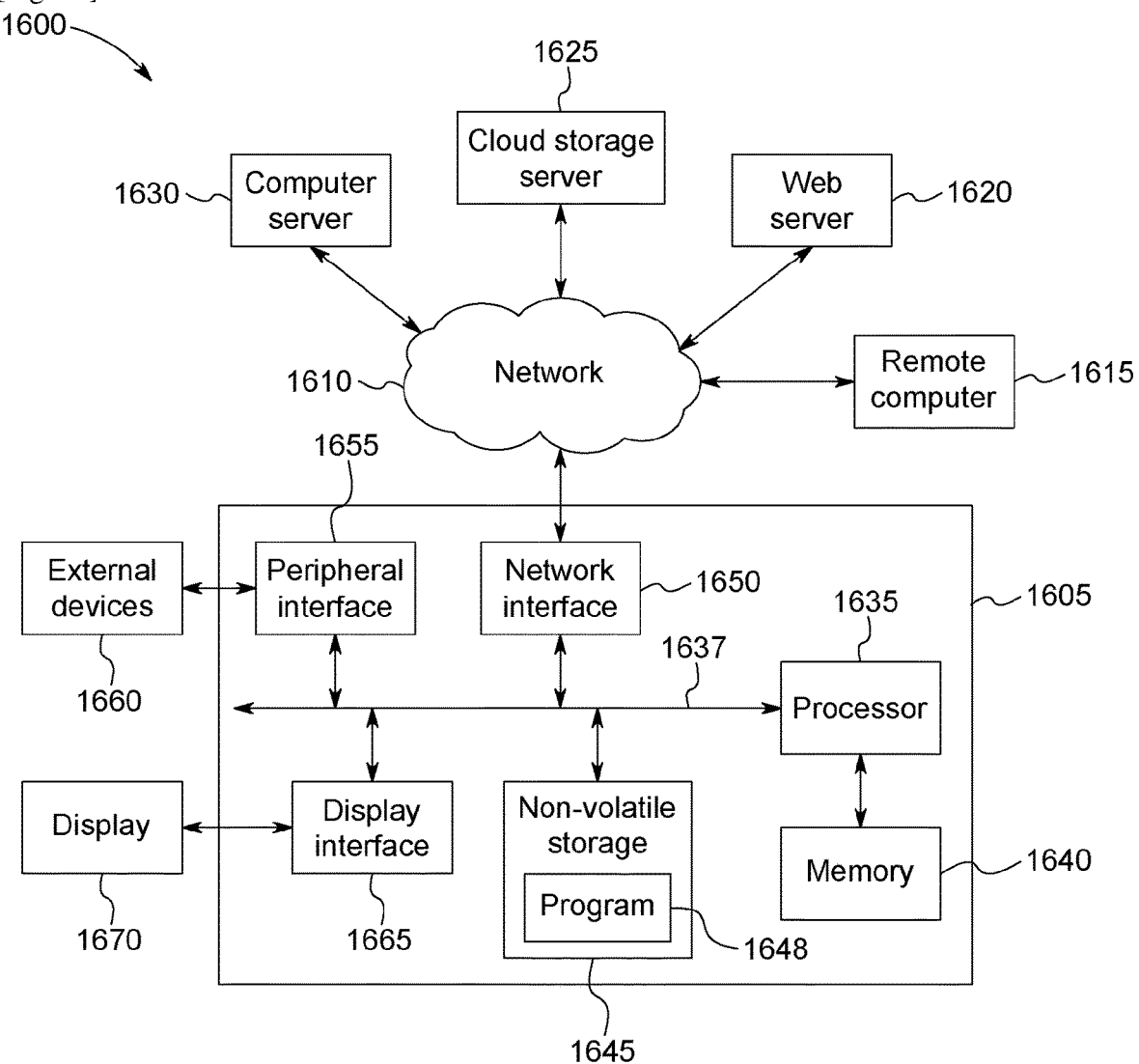

METHOD AND APPARATUS FOR STEREOSCOPIC COLOR EYE IMAGING

CROSS-REFERENCE TO RELATED APPLICATIONS

This application is based on PCT filing PCT/JP2020/034225, filed Sep. 10, 2020, which claims priority to U.S. Provisional Application Ser. No. 62/898,812 filed Sep. 11, 2019, the entire contents of each are incorporated herein by reference.

FIELD

The present disclosure relates generally to a method for ophthalmological imaging (e.g., stereoscopic color eye imaging), an apparatus for ophthalmological imaging, and a computer-readable medium for ophthalmological imaging.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Stereo disc photography has been used to document structural abnormalities and longitudinal changes in ophthalmology. For example, a stereoscopic color eye photo has been used for optic nerve head (ONH) imaging for analysis and diagnosis. In stereoscopic color eye photography, two images are created photographically and, when viewed, the two images may become fused in the brain of an observer to give the impression of depth. That is, when the observer views the two images, the observer's left eye views the left image, the observer's right eye views the right image, and the observer's brain recreates the depth relationships (or disparity) that were present at the time of photography.

Imaging technologies that provide topological information of the retina include traditional stereo-based topography, confocal scanning laser ophthalmoscope (cSLO), and optical coherence tomography. For example, the stereo-based topography uses a pair of images acquired from a traditional stereoscopic imager to computationally reconstruct the depth of retina. According to this conventional technique, a 3D depth profile can only be reconstructed by an observer's brain. In other word, it can only be assessed qualitatively. cSLO is an imaging technology that uses laser light to raster scan the retina, instead of a bright white flash used in standard eye or fundus cameras, which provides better comfort to the patient. The reflected light is then captured through a small aperture (confocal pinhole) blocking the scattered light, giving a sharp, better quality and high contrast image. Sequential cSLO scans captured at increasing depths can be combined to create three-dimensional topographic images of the retina or optic disc. Image stacks are aligned to create a final composite image to provide retinal thickness measurements of the macula or optic nerve head topography. Unfortunately, eye motion may degrade the quality of cSLO image due to relatively long imaging duration. This will result in increasing measurement error in 3D depth profile. Optical coherence tomography (OCT) is an imaging technique that uses low-coherence light to capture micrometer-resolution, two- and three-dimensional images from within optical scattering media (e.g., biological tissue). OCT is based on low-coherence interferometry, typically employing near-infrared light. From the OCT A-line profile (a backscattered optical signal at each depth), a depth information (or topological analysis) can be extracted computationally by segmenting the retinal layer on each OCT B-frame (multiple A-lines along scan axis). This approach has been widely used in clinic.

A Digital Light Ophthalmoscope (DLO) uses a confocal imaging technique such as described in U.S. Pat. No. 8,237,835. 2012. A digital light projector (DLP) based on a digital micromirror device (DMD) is configured to rapidly project a sequence of adjacent illumination lines across the field of view. Backscattered light from the target is de-scanned (i.e., multiple-scatter imaging) only to improve DLO contrast, and imaged directly onto a monochrome complementary metal oxide semiconductor (CMOS) sensor with a rolling shutter method of detection. In this configuration, the rolling shutter acts as a flexible electronic aperture, which can be finely adjusted in position and width through software in real-time.

A DMD for example as described in U.S. Pat. No. 5,061,049, is a micro-optoelectro-mechanical system (MOEMS). A DMD chip may have on its surface several hundred thousand microscopic mirrors arranged in a rectangular array which correspond to the pixels in the image to be displayed (or projected). The mirrors can be individually rotated ±10-12°, to an on or off state. In the on state, light from the projector bulb is reflected into the lens making the pixel appear bright on the screen. In the off state, the light is directed elsewhere (usually onto a heatsink or black body), making the pixel appear dark. The activation of each micro-mirror on a DMD can be controlled in real-time to project optical scanning beam to a given sample and to collect backscattered light from the same imaging sample.

CITATION LIST

Patent Literature

PTL 1: U.S. Pat. No. 5,061,049
PTL 2: U.S. Pat. No. 8,237,835. 2012
PTL 3: U.S. Pat. No. 6,758,564 B2

Non Patent Literature

NPL 1: Marshall E. Tyler, CRA, FOPS. Stereo Fundus Photography: Principles and Technique. Journal of Ophthalmic Photography, 1996;18(2):68-81

NPL 2: Muller M S, Elsner A E. Confocal Retinal Imaging Using a Digital Light Projector with a Near Infrared VCSEL Source. Proc SPIE Int Soc Opt Eng. 2018;10546:105460G. doi:10.1117/12.2290286

NPL 3: Elsner, A E., Petrig, B L. Laser Scanning Digital Camera with Simplified Optics and Potential for Multiply Scattered Light Imaging. U.S. Pat. No. 7,831,106. 2007.

NPL 4: Espina M P, Arcinue C A, Ma F, Camacho N, Bartsch D U, Freeman W R. ANALYSIS OF A CONFOCAL SCANNING LASER OPHTHALMOSCOPE NONCONTACT ULTRA-WIDE FIELD LENS SYSTEM IN RETINAL AND CHOROIDAL DISEASE. Retina. 2015;35(12): 2664-2668. doi:10.1097/IAE.0000000000000899.

NPL 5: Huang, D; Swanson, E A; Lin, C P; Schuman, J S; Stinson, W G; Chang, W; Hee, M R; Flotte, T; et al. (1991). "Optical coherence tomography". Science. 254 (5035): 1178-81.

NPL 6: Hansung Kim, Shinwoo Choi, Kwanghoon Sohn, "Real-time depth reconstruction from stereo sequences,"

Proc. SPIE 6016, Three-Dimensional TV, Video, and Display IV, 60160E (15 Nov. 2005).

NPL 7: J. Gu, Y. Hitomi, T. Mitsunaga and S. K. Nayar. Coded Rolling Shutter Photography: Flexible Space-Time Sampling. IEEE International Conference on Computational Photography (ICCP), March 2010.

NPL 8: Kafieh R, Rabbani H, Kermani S. A review of algorithms for segmentation of optical coherence tomography from retina. J Med Signals Sens. 2013;3(1):45-60.

NPL 9: Chen T C. Spectral domain optical coherence tomography in glaucoma: qualitative and quantitative analysis of the optic nerve head and retinal nerve fiber layer (an AOS thesis). Trans Am Ophthalmol Soc. 2009;107:254-281.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

According to an aspect of the present disclosure, an ophthalmological imaging device includes illumination optics including an illumination light source configured to output an illumination light, a scanner configured to receive the illumination light from the illumination optics, and redirect the illumination light toward a portion of an object to be imaged, an optical image capture device including a camera configured to receive backscattered light that is scattered from the illumination light by the object and capture first and second images of the backscattered light, a control processor configured to control the scanner and the optical image capture device to cause the optical image capture device to capture the first and second images of the object, the first and second images being captured by the camera at different times and extracted from different portions of the backscattered light, and an image processor configured to generate a stereoscopic image from the first and second images of the object.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein:

FIG. 1 schematically illustrates a block diagram of a stereoscopic color eye imaging apparatus according to an embodiment of the invention.

FIG. 2A illustrates an example of acquisition angle change with an upper and lower view acquisition scheme according to an embodiment of the invention.

FIG. 2B illustrates an example of acquisition angle change with a left and right view acquisition scheme according to an embodiment of the invention.

FIG. 2C depicts an example of an operation of an illumination and detection scheme according to an embodiment of the invention.

FIG. 2D shows an example of optical tracing according to an embodiment of the invention to further illustrate how field of view angle and stereoscopic viewing angle are related different.

FIG. 2E shows an example of an operation of an embodiment of the invention with dynamic aperture at a pupil plane.

FIG. 2F shows an example of an operation of an embodiment of the invention with dynamic aperture change (split aperture case).

FIG. 2G shows an example of an embodiment of the invention using a dynamic aperture.

FIG. 2H shows an example of an embodiment of the invention using an aperture stop setting.

FIG. 2I shows an example of an embodiment of the invention using a split aperture.

FIG. 2J shows an example of a narrow viewing angle in a split aperture setting according to an embodiment of the invention.

FIG. 2K shows an example of a wide viewing angle in a split aperture setting according to an embodiment of the invention.

FIG. 3A illustrates an example of viewing angle change with a narrow viewing angle at aperture stop setting according to an embodiment of the invention.

FIG. 3B illustrates an example of viewing angle change with a wide viewing angle according to an embodiment of the invention.

FIG. 4A illustrates an example of optical field of view (FOV) change with a wide FOV at an aperture stop setting according to an embodiment of the invention.

FIG. 4B illustrates an example of FOV change with a narrow FOV at an aperture stop setting according to an embodiment of the invention.

FIG. 4C illustrates an example of imaging field of view increase by acquiring and mosaicking a series of images.

FIG. 4D illustrates an example of scan direction change.

FIG. 5 illustrates an example of a stereoscopic color eye imaging apparatus including a 2D camera with rolling shutter mechanism plus galvo scanner according to an embodiment of the invention.

FIG. 6A illustrates an example of galvo and detector upper view control signals according to an embodiment of the invention.

FIG. 6B illustrates an example of galvo and detector lower view control signals according to an embodiment of the invention.

FIG. 6C shows an operational example of an embodiment of the invention to further illustrate how changes in the galvo scanner control voltage affect the scanning angle (or illumination angle).

FIG. 7A illustrates an example of upper view control signals during narrow viewing angle dynamic viewing angle change on a galvo scanner-based imaging apparatus according to an embodiment of the invention.

FIG. 7B illustrates an example of lower view control signals during narrow viewing angle dynamic viewing angle change on a galvo scanner-based imaging apparatus according to an embodiment of the invention.

FIG. 7C illustrates an example of upper view control signals during wide viewing angle dynamic viewing angle change on a galvo scanner-based imaging apparatus according to an embodiment of the invention.

FIG. 7D illustrates an example of lower view control signals during wide viewing angle dynamic viewing angle change on a galvo scanner-based imaging apparatus according to an embodiment of the invention.

FIG. 8 illustrates an example of a stereoscopic color eye imaging apparatus including 2D camera with rolling shutter mechanism plus DMD according to an embodiment of the invention.

FIG. 9A illustrates an example of DMD and detector upper view control signals.

FIG. 9B illustrates an example of DMD and detector lower view control signals.

FIG. 10A illustrates an example of upper view control signals during narrow viewing angle dynamic viewing angle change on a DMD-based imaging according to an embodiment of the invention.

FIG. 10B illustrates an example of lower view control signals during narrow viewing angle dynamic viewing angle change on a DMD-based imaging according to an embodiment of the invention.

FIG. 10C illustrates an example of upper view control signals during wide viewing angle dynamic viewing angle change on a DMD-based imaging according to an embodiment of the invention.

FIG. 10D illustrates an example of lower view control signals during wide viewing angle dynamic viewing angle change on a DMD-based imaging according to an embodiment of the invention.

FIG. 11A illustrates an example of a stereoscopic color eye imaging apparatus including a multiple-scan camera plus galvo scanner according to an embodiment of the invention.

FIG. 11B illustrates an example of operation of the embodiment in FIG. 11A at an aperture stop setting.

FIG. 12A illustrates an example method of stereoscopic imaging using parallel stereo acquisition according to an embodiment of the invention.

FIG. 12B illustrates an example method of stereoscopic imaging using converging stereo acquisition according to an embodiment of the invention.

FIG. 12C illustrates an example of operation of stereoscopic imaging according to an embodiment of the invention.

FIG. 13 illustrates an example of a method of stereoscopic imaging with 3D visualization and analysis processing performed using a processing unit according to an embodiment of the invention.

FIG. 14A illustrates an example of stereoscopic color eye images according to an embodiment of the invention.

FIG. 14B illustrates a three dimensional plot of information extracted from the stereoscopic color eye images in FIG. 14A according to an embodiment of the invention.

FIG. 15A illustrates a three dimensional plot of information including a cup depth estimation performed according to an embodiment of the invention.

FIG. 15B illustrates a three-dimensional plot of information including a cup to disc ratio estimation performed according to an embodiment of the invention.

FIG. 16 illustrates an example of a computer structure that may be used to implement portions of the invention according to an embodiment of the invention.

Further areas of applicability of the present disclosure will become apparent from the detailed description provided hereinafter. It should be understood that the detailed description of exemplary embodiments is intended for illustration purposes only and are, therefore, not intended to necessarily limit the scope of the disclosure.

DETAILED DESCRIPTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Control methods and systems described herein may be implemented using computer programming or engineering techniques including computer software, firmware, hardware or any combination or subset thereof.

Age related macular degermation (AMD) and glaucoma are the major causes of blindness in ophthalmology. Many eye exams have been developed to assess these types of diseases such as clinical slit lamp exam and imaging. Recently, OCT devices have been employed to image and visualize these types of eye diseases in near real-time. Unfortunately, the OCT device is relatively expensive, and a trained operator or technician is required to operate the OCT device. Thus, OCT device-based exams are expensive, which may partially explain why OCT device-based exams are not commonly used in less developed countries or rural areas.

The present disclosure relates to a stereoscopic color eye imaging apparatus, method, and computer-readable medium that includes reconstruction of a 3D depth profile from the resulting stereoscopic color eye image and that may overcome existing limitations. Any desired portion of the eye may be imaged, including the fundus of the eye. The invention is also applicable to imaging other portions of human anatomy. The term "stereoscopic color eye imaging apparatus" and "stereoscopic color fundus imaging apparatus" used to describe embodiments of the invention should be considered equivalent. A stereoscopic color fundus imaging apparatus according to an embodiment of the invention may include a light source unit, detector/sensor unit, scanner unit, imaging optics, and control unit, which operate to provide stereoscopic images and information, which may be useful for screening eye diseases in ophthalmology. Additionally, the stereoscopic color fundus imaging apparatus and method described herein can provide images, optical resolution, and features comparable to those produced by conventional DLO, cSLO, or line-scan SLO (e.g., as described in U.S. Pat. No. 6,758,564 B2) while avoiding or minimizing the disadvantages in those prior art approaches.

An embodiment of the invention may result in a relatively low-cost system compared to an OCT based device. Such an embodiment may be partially or fully automated (e.g., easy to operate like taking a selfie) or may only require minimum training for imaging. People living in remote areas and in less developed countries will be able to take full advantage of this invention.

An embodiment of a stereoscopic color fundus imaging apparatus and method according to the present invention may analyze the retina stereoscopically and can provide imaging features comparable to a conventional color fundus imager at a lower cost and with easier operation. According to an embodiment of the invention, a multiple scattering signal (backscattered light to the upper portion and the lower portion) may be used to reconstruct a 3D depth profile (i.e., to perform stereoscopic imaging) by calculating a disparity between first and second images comuptationally and dynamically.

FIG. 1 illustrates an example schematic of a stereoscopic color fundus imaging apparatus that can obtain a stereoscopic color image of the fundus of an eye 116. The apparatus in this embodiment includes imaging optics 102, optical scanner unit 110, control unit 104, detector/sensor unit 112, processing unit 106, display unit 108, and storage unit 114. In addition, the apparatus according to alternative embodiments may capture gray scale stereoscopic images of the fundus of the eye 116 instead of color stereoscopic images of the fundus of the eye 116.

The imaging optics 102 may include optical components such as a light source, optical lens, holders and optical aligning tools, and optical shutter. One or more halogen lamp and/or LED may be used as the light source. The optical scanner unit 110 may redirect optical illumination light from the imaging optics to a sample or object to be imaged (e.g., an eye) and receive backscattered light scattered from the sample or object to be imaged at the same time. The control unit 104, which may be implemented using a general purpose computer programmed for functions as described below, controls operation of all the electrical and mechanical parts and units in the system. To achieve a stereoscopic view, at least two or more images are acquired with enough viewing angle difference between the two or more images. According to an embodiment of the invention, the image acquisition angle can be set arbitrarily, but its scan direction may advantageously be perpendicular to a detector shutting direction, for example, to best utilize a rolling shutter camera mechanism according to one example as described below with respect to FIGS. 2A, 2B, 2C, and 2D. Furthermore, a fixation target from the control unit can be provided to assist optical focusing/alignment and suppress eye motion.

The relative distance between the optical scanning position and the detection location can be dynamically changed to introduce and/or vary the stereoscopic viewing angle difference as discussed below with respect to FIGS. 3A and 3B. To complete the stereoscopic imaging, at least two images (e.g., scan #1 208a and scan #2 208b in FIG. 2A; or scan #1 208c and scan #2 208d in FIG. 2B; or scan #1 308a and scan #2 308b in FIG. 3A; or scan #1 308c and scan #2 308d in FIG. 3B) should be acquired with different viewing angles.

According to an embodiment of the invention, stereoscopic imaging may be performed using : 1) a split aperture operation, and 2) an aperture stop operation. According to an embodiment of the invention, an optical aperture in the imaging optics can be changed dynamically between a split aperture mode and an aperture stop mode. Examples of such a dynamic change between split aperture and aperture stop operation, are shown during imaging of eye 276 in FIG. 2E. In the example of FIG. 2E, illumination is performed through the center portion of the eye and the detection is annular. In the aperture stop mode, the illumination is in an annular portion of the eye and the detection is through the center portion of the eye. In the example of FIG. 2E, in a split aperture case, with a horizontal aperture, illumination 270 is ~φ2.0 mm, d 272 is ~0.5 mm, and detection width 274. Illumination of the eye 276 using a vertical aperture is also shown for the split aperture case. FIG. 2E also shows an aperture stop case in which detection 280 is ~φ2.0 mm, d 278 is ~0.5 mm, illumination width 282 is ~0.5 mm. Illumination of the eye 276 is also shown for the vertical aperture/aperture stop case. Thus, parameters dynamically controlled by the control unit 104 include aperture, optical magnification, and viewing angle.

FIG. 2F shows further detail regarding an operation during a split aperture mode. According to an embodiment of the invention in the split aperture case, using a horizontal aperture (i.e., in upper portion of FIG. 2F), aperture switching can be performed to introduce a viewing angle by switching from an upper view scan of eye 284 (i.e., in upper left of FIG. 2F, producing a first optical image 286) to a lower scan view of the eye 284 (i.e., in upper right of FIG. 2F, producing a second optical image 288). Alternatively, when using a vertical aperture, the viewing angle difference between first optical image 290 and second optical image 292 is created by switching between a left view scan (i.e., lower left of FIG. 2F) and a right view scan (i.e., lower right of FIG. 2F). In the split aperture mode, the illuimination and detection location can be identical. The difference in vieweing angle can be introduce by switching from upper aperture to lower aperture at a pupil plane, or from left aperture to right aperture at a pupil plane. Therefore, a time delay between illumination and detection (unlike in aperture stop mode) is not needed in the split aperture mode stereoscopic imaging because the viewing angle difference is introduced by switching aperture shape (upper view aperture←→lower view aperture). When the aperture setting is at an aperture stop, the viewing angle difference between the scanned images can be increased or decreased by changing the relative distance between an optical scanning position (e.g., illumination/scanning positions 204a and 202b, 204c and 202d in FIGS. 2A and 2B, and 304a, 302b, 304c, and 302d in FIGS. 3A and 3B) and a detection location (e.g., detection locations 202a, 204b, 202c, and 204d in FIG. 2A and 2B, and 302a, 304b, 302c, and 304d in FIGS. 3A and 3B). The optical scanning position is the location on the fundus of the eye where the optical scanning beam (i.e., a line of illumination light projected on the fundus of the eye by the apparatus) is projected and the detection location is a corresponding position on the imaging plane (e.g., camera sensor surface) at which the optical backscattered light is projected. When the optical magnification factor is equal to 1×, the physical scale between imaging plane and fundus plane should be identical. Variation in the viewing angle difference is achieved according to an embodiment of the invention by changing a relative time interval (i.e., leading or lagging time) between an optical scanner control signal that selects a line of fundus eye to capture an image and image acquisition control signal (line-by-line acquisition).

When the optical scanning beam is projected on the eye fundus by a galvo scanner (e.g., galvo scanner 510), a galvo control signal is generated from the control unit 104 to control the galvo scanner. The galvo control signal is controlled by the control unit 104 based on parameters including optical magnification, camera frame rate, required depth resolution, and FOV. The parameters may be predetermined and stored in memory (e.g., storage unit 114), may be set dynamically by a user interface on the control unit 104 or processing unit 106, or may be controlled by a remote operator using another computer connected to the control unit 104 or processing unit 106. The galvo control signal is particularly designed to control the projection angle of optical scanning beam relative to an imaging sample. In general, the amount of projection angle change is linearly proportional to the analog voltage of the galvo control signal (excluding a DC voltage offset in the signal). For example, when the wide FOV imaging is required, the voltage of the galvo control signal should increase proportionally, as compared with the narrow FOV imaging. In parallel, the backscattered light from an imaging sample will be reflected from the galvo scanner's mirror surface, then digitized by the detector (i.e., camera sensor). The digitization is done using a 2D camera with rolling shutter mechanism so that each row of the detector array on the 2D camera will be sequentially triggered by a camera trigger control signal generated by the control unit 104 to digitize the incoming optical signal received by the corresponding line of pixels on the camera sensor. In traditional SLO imaging, a detection location should be equal to the scanning beam position to achieve optimum signal to noise ratio. However, in stereoscopic imaging according to an embodiment of the invention, the detection location relative to the scanning beam position should be off-center for stereoscopic views. The amount of off-centering on the image plane (or camera) can be expressed in time scale because the line-by-line acquisition of 2D camera and the incremental galvo control signal voltage change are controlled by the control unit 104 at a fixed rate (frequency). Therefore, a viewing angle in the dynamic stereoscopic image produced by the processing unit 106 can simply be controlled by the control unit 104 introducing a relative phase shift between 2D camera trigger control signal and the galvo control signal. The resulting stereoscopic viewing angle between two consecutive images (stereo images) will determine the minimum resolvable depth resolution obtained by analyzing the images. Therefore, the control unit 104 may synchronize operation of the optical scanner unit 110 and the detector/sensor unit 112 to achieve an ideal depth resolution. A polygon scanner can also be used instead of galvo scanner.

An optical magnification of the stereoscopic image produced by an embodiment of the invention can affect not only the optical field of view but also the resolvable stereoscopic depth resolution. The greater the optical magnification, the greater the resolvable stereoscopic depth resolution.

The detector/sensor unit 112 includes a digitizer/sensor to convert backscattered light to electrical signals. The digitizer may include a charge coupled device (CCD) camera with rolling shutter, multiple-line scan camera, or any other readily available two-dimensional image sensing device. The control unit 104 controls all the system components including optical magnification control, execution of user control commands, auto alignment/focus, galvo/DMD control, and safety mechanism, real-time optical power/spectrum monitoring, and real-time eye tracking. The processing unit 106 includes a processing circuit configured by software, firmware, and/or hardware to calculate, process, and extract stereoscopic information from the captured images. The processing unit 106 handles user applications such as image reconstruction analysis, cloud-based services, patient information, and clinical recording. One or both of the processing unit 106 and the control unit 104 further includes a user interface allowing a user to control parameters and operation of the apparatus and/or method. The user interface is configured to provide instructions and/or control feedback (including visual and/or auditory cues) instructing a user in proper user of the apparatus and/or method. One or both of the processing unit 106 and the control unit 104 includes a communication interface allowing the images to be input from other imaging sources, and allowing processing results to be output electronically (e.g., to share with a patient or a medical professional), and to allow portions or the entirety of the control and processing functions described herein to be performed by a remote, network attached, and/or cloud based computer. The display unit 108 includes a projector, monitor, display, or printer which can be used by a user to visualize the information produced by the processing unit 106. The storage unit 114 is a digital storage memory configured to store information such as the captured images, 3D reconstructed data, clinical records, operating programs for the processing unit 106, control unit 104, and configuration data for the apparatus or method.

FIG. 2A illustrates an example of acquisition angle change with an upper and lower view acquisition scheme in an aperture stop mode according to an embodiment of the invention. In this example, "upper" and "lower" refer to the different directions from which the viewing angle is varied. However, this is merely an exemplary pair of directions and other directions are also within the scope of the invention, such as 10 o'clock and 4 o'clock, or 11 o'clock and 5 o'clock, 7 o'clock and 1 o'clock, etc. . . . so that the first and second images are received at different scattering angles from the object, where the scattering angles are separated from each other by 180 degrees. A sensor (such as a CCD image sensor) is configured to capture a detection line 202*a* (i.e., a line of pixels from the sensor) on a fundus of an eye 208*a* that is focused on by the sensor while an illumination line 204*a* illuminates another portion of the fundus of the eye 208*a*, and while the detection line 202*a* and the illumination line 204*a* are moved in the scanning direction 206*a* (by a scanner described below) along the fundus of the eye 208*a* to capture a first (upper view) color fundus image 210*a*. The position of the illumination line 204*a* (i.e., the portion illuminated by the apparatus) is separated from the detection line 202*a* (i.e., the position of the region captured in an image by the apparatus) by a distance that is predetermined or controllable by the control unit based on the processes discussed in greater detail below. A lower view is captured by detection line 204*b* and illumination line 202*b* that are controlled to move across the fundus of the eye 208*b* (the same eye as in 208*a*) to capture a second (lower view) color fundus image 210*b*.

FIG. 2B illustrates an example of acquisition angle change with a left and right view acquisition scheme at aperture stop mode according to an embodiment of the invention. This example operates similar to the example in FIG. 2A; however, in FIG. 2B, the viewing angle difference is captured in the left/right direction as opposed to the upper/lower direction in FIG. 2A. Thus, according to the example of FIG. 2B a left view is performed by a detection line 202*c* and illumination line 204*c* that move in the scanning direction 206*c* across the fundus of eye 208*c* to produce a first (left view) color fundus image 210*c*. According to this example, a right view is performed by detection line 204*d* and illumination line 202*d* that move in the scanning direction 206*d* across the fundus of eye 208*d* to capture a second (right view) color fundus image 210*d*.

FIG. 2C depicts an example of an operation of an illumination and detection scheme according to an embodiment of the invention. As shown in FIG. 2C, an illumination light 236 illuminates the fundus of an eye 220 through a center of a pupil plane. Backscattered light 230 from the illuminated eye 220 is spread across a backscattering angle 238 and is received by a focusing lens 232 and beam splitter 234 (included in the imaging optics 102). A galvo scanner 224 redirects the backscattering light 230 to a rolling shutter camera 222. A dynamic aperture component (e.g., aperture wheel rotatable to select different fixed sized apertures, or a controllable aperture having a variable aperture opening sizes) may be used to switch between different apertures such as split aperture mode and aperture stop mode. A portion of the backscattered light 230 that scatters in a first direction 226 is used to capture a first color fundus image from a first viewing angle (e.g., upper viewing angle to capture color fundus image 210*a* in FIG. 2A, or left viewing angle to capture color fundus image 210*c* in FIG. 2B) and another portion of the backscattered light 230 that scatters in a second direction 228 (where first direction 226 and second direction 228 are separated by 180 degrees) is used to capture a second image from a second viewing angle (e.g., lower viewing angle to capture color fundus image 210*b* in FIG. 2A, or right viewing angle to capture color fundus image 210*d* in FIG. 2B). Thus, the backscattered light 230 in this example is digitized by a detector array to produce a pair of viewing angle separated images (i.e., upper/lower images or left/right images). The same sensor may capture the first and second images at a different timing (e.g., either before or after a timing of the capture of the first color fundus image), for example, using an illumination line 202*b* and detection line 204*b* moved in scanning direction 206*b* to capture a second color fundus image 210*b* of the fundus of the eye 208*b*.

FIG. 2D shows an example of optical tracing according to an embodiment of the invention to further illustrate how the FOV and stereoscopic viewing angle are related. In the example of FIG. 2D, illumination light 236 illuminates eye 220, which scatters backscattered light 230 at a backscattering angle 238 which corresponds to a viewing angle difference between first and second (e.g., upper and lower) captured images. The backscattered light 230 is received by focusing lens 232, scanner DMD 240, dynamic aperture at aperture stop mode, and rolling shutter camera 244 to produce an upper view from backscattered portion 226 and a lower view from backscattered portion 228. The upper view portion 226 corresponds to a detection location 258 and a related illumination line 260 when the scan in the scanning direction 262 across the fundus of the eye 248 to produce the upper view scan (i.e., first captured image). The lower view portion 228 corresponds to a detection location 266 and the related illumination line 264 as they move in the scanning direction 268 across the fundus of the eye 250 to capture a second image. A distance between the detection line 258 and the detection line 266 corresponds to a base line distance and to a time delay (e.g., time delay 608*a* described below). A region over the fundus of the eye 250 that is captured corresponds to a horizontal FOV 252 and a vertical FOV 256. The first (upper) scan and the second (lower) scan may be captured 40 ms apart as indicated by elapsed time 246. The narrow/wide viewing angle discussed further in the examples below is related to the field of view (FOV) of imaging. FOV is a maximum imaging window size, while viewing angle means a stereoscopic viewing angle. Thus, in the examples of FIGS. 3A and 3B, the stereoscopic imaging pairs (i.e., first and second captured images) are captured while varying the viewing angle from narrow to wide angle. The wide/narrow viewing angle is varied under control of the control unit 104 while using an actuator/motor that is included in the imaging optics 102 or optical scanner 110 or detector/sensor unit 112 to change the wide/narrow viewing angle.

FIG. 2G shows an example of an embodiment of the invention including many elements in common with the embodiment shown in FIG. 2C, but with the addition of a dynamic aperture component 294 (e.g., aperture wheel or controllable aperture) configured to operate according to the dynamic aperture switching modes.

FIGS. 2H and 2I show examples of obtaining a viewing angle change between captured images in an aperture stop mode (FIG. 2H) and in a split aperture mode (FIG. 2I) according to an embodiment of the invention. In these example, an eye 2102 is illuminated by an illumination light 2110, and backscattering light 2104 spread at a viewing angle 2106 is received by a focusing lens 2108, and galvo/DMD 2118. The backscattered light is further received by an aperture stop 2112 (in the example of FIG. 2H) or a split aperture 2114 (in the example of FIG. 2I), an optical magnifier 2116, and a rolling shutter camera 2120 having a detector surface 2126. In the example of FIG. 2H, using an aperture stop 2112 in aperture stop mode, a point spread function (PSF) at the detection surface 2126 of the camera 2120 includes an upper view 2132 and a lower view 2130, as shown overlaying intensity plot 2128. In the example of FIG. 2I, using a split aperture 2114 in split aperture mode, a PSF at the detection surface 2126 of the camera 2120 includes an upper/lower view 2134/2136 as shown overlaying intensity plot 2138. In the split aperture mode, the illumination and detection location should be identical. The difference in viewing angle in the split aperture mode is obtained by switching from upper aperture to lower aperture a the pupil plane, or from left aperture to right aperture at the pupil plane, as illustrated by FIG. 2F.

FIG. 2J shows an example of narrow view angle capture in the split aperture setting mode. In this example, using a horizontal aperture, an upper view scan on eye 2204 is performed to capture a first optical image 2206, and after aperture switching, a lower view scan on eye 2204 is performed to obtain a second optical image 2208. Offset d 2202 is ~0.2 mm.

FIG. 2K shows an example of wide viewing angle capture in split aperture setting mode. In this example, using a horizontal aperture, an upper view scan of eye 2204 is performed to capture a first optical image 2210, and after aperture switching, a lower view scan on eye 2204 is performed to obtain a second optical image 2212. Offset d 2214 is ~0.6 mm. Use of a vertical aperture is alternatively possible in the examples of FIGS. 2J and 2K.

FIG. 3A illustrates an example of viewing angle change with a narrow viewing angle at aperture stop settting according to an embodiment of the invention. In this example, the camera sensor is configured to capture an upper view with narrow field of view using a detection line 302*a* and illumination line 304*a* that are controlled to move in the scanning direction 306*a* along the fundus of the eye 308*a* to capture a first (upper view/narrow field of view) color fundus image 310*a*. The same sensor, at a different time either before or after the capture described above, captures a lower view with the narrow FOV using a detection line 304*b* and illumination line 302*b* that are controlled to move across the fundus of the eye 308*b* to capture a second (lower view/narrow field of view) color fundus image 310*b*. To reconstruct three dimensions, at least two images with different viewing angle are required in stereoscopic imaging. The imaging field of view, which is determined by user in general, needs to be identical between these images.

FIG. 3B illustrates an example of viewing angle change with a wide field of view at an aperture stop settting according to an embodiment of the invention. In this example, the camera sensor is configured to capture an upper view with wide field of view using a detection line 302*c* and illumination line 304*c* that are controlled to move in the scanning direction 306*c* along the fundus of the eye 308*c* to capture a first (upper view/wide field of view) color fundus image 310*c*. The same sensor captures a lower view of the same eye with wide field of view using a detection line 304*d* and illumination line 302*d* that are controlled to move in the scanning direction 306*d* along the fundus of the eye 308*d* to capture a second (lower view/wide field of view) color fundus image 310*d*. The capture of first and second images from different viewing angles at constant narrow or wide field of view provides the ability to view different regions of the fundus of the eye in three-dimensions and with controlled resolution and/or depicting larger or smaller area of interest, and different lighting angles.

FIG. 4A illustrates an example of optical field of view (FOV) change with a wide FOV in aperture stop mode according to an embodiment of the invention. FIG. 4B illustrates an example of FOV change with a narrow FOV according to an embodiment of the invention. The examples of FIGS. 4A and 4B are similar to those in FIGS. 3A and 3B, respectively, except that where FIGS. 3A and 3B show a change in viewing angle from a first pair of captured images to a second pair of captured images. When the aperture setting is at split aperture mode, the FOV change is identical except the difference in acquisition scheme is as described above in FIG. 2F. FIGS. 4A and 4B show a change in field of view angle and a change in scanning direction from a first pair of captured images to a second pair of captured images. Thus, in the examples of FIGS. 4A and 4B, the stereoscopic imaging pairs are captured with wide and narrow field of view. The wide/narrow FOV is varied under control of the control unit 104 while using an actuator/motor included in one or more of the imaging optics 102, optical scanner 110, and detector/sensor unit 112 to change the wide/narrow FOV. Thus, according to the example of FIG. 4A, a first scan of an upper view with a wide FOV angle is captured using a detection line 402a and illumination line 404a that are controlled to move across the fundus of eye 408a in the scanning direction 406a to capture a first (upper viewing angle/wide FOV angle) color fundus image 410a. The same sensor may capture a scan of a lower view with the wide FOV angle using a detection line 404b and illumination line 402b that are controlled to move across the fundus of the eye 408b in the scanning direction 406b to capture the second (lower viewing angle/wide FOV angle) color fundus image 410b.

According to the example of FIG. 4B, a first scan of a left view with a narrow FOV angle is captured using a detection line 402c and illumination line 404c that are controlled to move in the scanning direction 406c across the fundus of the eye 408c to capture a first (left view/narrow FOV angle) color fundus image 410c. The same sensor may capture a scan of a right view with the narrow FOV angle using a detection line 404d and illumination line 402d that are controlled to move across the fundus of the eye 408d in the scanning direction 406d to capture the second (right view/narrow FOV angle) color fundus image 410d.

According to an embodiment of the invention, the time between the first and second images may advantageously be less than 100 ms and preferably 40 ms to thereby reduce the possibility of eye motion between the first and second images and as a result to improve the accuracy of a three-dimensional image created based on the first and second images. The time between the first and second images may decrease as the acquisition speed of detector increases.

As shown in the example of FIG. 4C, the imaging field of view can also be increased by acquiring and mosaicking a series of images 412, 414, 416, and 418 by shifting the center position of imaging field of view (or region of interest) for each image and combining the separate images to form a mosaicked image having a larger field of view than any of the individual images. A dynamic change in the region of interest can be done by user interface or the control unit.

Additionally, as shown in the example of FIG. 4D, the scan direction can be changed according to user preference. In the example of FIG. 4D, fundus 428 may be imaged in scanning direction 426 using illumination line 422 and detection line 424 to capture a first scan (e.g., a lower view color fundus image) as shown in the top left of FIG. 4D. Fundus 428 may be imaged in scanning direction 434 (which is the same direction as scanning direction 426) using illumination line 432 and detection line 430 to capture a second scan (e.g., an upper view color fundus image) as shown in the bottom left of FIG. 4D. Alternatively, the scan direction can be reversed, and fundus 428 may be imaged in scanning direction 440 (which is an opposite direction from scanning directions 426 and 434) using illumination line 438 and detection line 436 to capture a first scan (e.g., an upper view color fundus image) as shown in the top right of FIG. 4D. Fundus 428 may be imaged in scanning direction 446 (which is the same direction as scanning direction 440) using illumination line 442 and detection line 444 to capture a second scan ((e.g., a lower view color fundus image) as shown in the bottom right of FIG. 4D. At split aperture mode, scan direction can be changed by switching aperture shape (upper view aperture←→lower view aperture), for example as shown in FIGS. 2E, 2F, 2H, and 2I.

FIG. 5 illustrates an example schematic of a stereoscopic color fundus imaging apparatus according to one embodiment that includes a detector/sensor unit implemented as a 2D camera with a rolling shutter mechanism. This embodiment includes imaging assembly 502 a detector/sensor unit 504, projection optics 508, a scanner 510, and illumination optics 512. The imaging assembly 502, which is part of the imaging optics 102, includes lenses (e.g., relay lenses) 502a, a dynamic aperture mirror 502b, and an objective lens 502c. The detector/sensor unit 504 includes the 2D camera with the rolling shutter mechanism 504a. The projection optics 508, which is an additional part of the imaging optics 102, includes lenses 508c, a black dot mask 508a, and a minor 508b. The illumination optics 512 includes lenses 512a (e.g., relay lenses), a slit 512b, an iris aperture 512c, a cylindrical lens 512d, and an illumination light source 512e. Also included in this embodiment are control unit 104, processing unit 106, display unit 108, and storage unit 114. The illumination light source 512e may include an LED, halogen lamp, or other known light source.

According to this embodiment, the illumination optics 512 outputs an illumination light produced by the illumination light source 512e. The scanner 510 receives the illumination light from the illumination optics 512, redirects an optical axis of the illumination light and outputs redirected illumination light. The projection optics 508 includes a minor 508b, which may be implemented using a digital light projector (DLP) and the projections optics 508 are configured to receive the redirected illumination light from the scanner 510 and output a projected light. The scanner may be implemented using a galvo mechanical scanner. A galvo scanner is an ammeter that indicates it has sensed an electric current by deflecting a light beam with a mirror. In general, the galvo scanner is used to project a scanning beam (i.e., an illumination line) to a given sample/eye region. The imaging optics 502 includes the dynamic aperture mirror 502b that receives and redirects the projected light through objective lens 502e towards the eye 506. Backscattered and reflected light from the eye 506 is received by the imaging optics 502 and provided to the detector/sensor unit 504 where it is captured by the 2D camera with the rolling shutter mechanism 504a.

The control unit 104 controls the operation and timing of each of various parameters in the apparatus including the an aperture size/pattern, exposure timing, sensor gain/sensitivity, focus of imaging optics, focus of illumination optics, focus of projection optics, direction and timing of scanner, capture timing of camera/sensor, orientation of DLP/mirror 508b, intensity and timing of illumination light, and optical magnification of each element in the apparatus. The processing unit 106 receives the images captured by the 2D camera with the rolling shutter mechanism 504a and performs processing as discussed further below to generate the stereoscopic color fundus image.

To obtain a stereoscopic image, optical scanning with controlled and varied viewing angles is achieved according to this embodiment, using the mechanical galvo scanner. The embodiment in FIG. 5 is configured to operate according to each of the examples shown in FIGS. 2A, 2B, 3A, 3B, 4A, and 4C. The operation is controlled according to predetermined commands stored in the storage unit 114, according to commands provided by user interface on the control unit 104 or processing unit 106, or according to commands received from a remote location by the control unit 104 or processing unit 106.

FIG. 6A illustrates an example of galvo scanner and detector upper view control signals according to an embodiment of the invention. In this example, galvo scanner control signal 604a, which corresponds to the voltage applied to the galvo scanner mirror, is plotted as applied scanner voltage 602a on the y-axis (e.g., 0-5 volts) with respect to time 606a (e.g., 0-50 ms) on the x axis. The voltage of the galvo scanner control signal determines the scanning beam (i.e., illumination line) position on the fundus of the eye. When the dynamic aperture setting is a split aperture mode, a constant time delay between illumination and detection (608a, 608c, 638, 708a, 708b, 708c, and 708d) is zero because the viewing angle difference is introduced and controlled by switching the upper and lower view apertures. Therefore, the stereoscopic image acquisition speed is relatively faster than the aperture stop based stereoscopic imaging mode, in which the time delay between illumination and detection is greater than zero. When the dynamic aperture setting is at an aperture stop mode, a viewing angle has to be introduced with respect to time. For example, a constant time delay (corresponding to the viewing angle) is shown by arrow 608a. The corresponding detector/sensor control signals used to turn on/off the sensor capture are also plotted at the same time scale on the x-axis 606a and with detector/sensor control signal voltage 602b on the y-axis. Each "on" timing of the detector/sensor control signal 610b, 612b, and 614b, is delayed by the time delay 608a and corresponds to capture of a line of images by a successive detector row (i.e., row 1 captured by detector/sensor control signal 610b, row 2 captured by detector/sensor control signal 612b, and row 3 captured by detector/sensor control signal 614b). As shown by this example, the successive rows are captured while the galvo scanner control signal voltage increases in voltage 602a, corresponding to a change in galvo scanner angle.

FIG. 6B illustrates an example of galvo and detector lower view control signals according to an embodiment of the invention. The example of FIG. 6B is similar to the example of FIG. 6A except that FIG. 6B shows the lower view control signal timing as opposed to the upper view control signal timing in FIG. 6A. In FIG. 6B, the galvo scanner control signal is controlled to have an increasing voltage 602c over time 606c after a constant time delay 608c that corresponds to a desired viewing angle difference between the upper and lower views. The desired viewing angle may be predetermined and stored in the storage unit 114, may be set according to a user interface instruction, or set remotely. Image capture is controlled by the control unit 104 which outputs control signal voltage 602d varying over time 606c, without waiting for the time delay 608c, to control capture by sensor row numbers 1-6 (i.e., 610d, 612d, 614d, 616d, 618d, and 620d). Thus, in this example, the time delay corresponds to a viewing angle difference between the upper view scan in FIG. 6A and the lower view scan in FIG. 6B.

FIG. 6C shows an operational example of an embodiment of the invention to further illustrate how changes in the galvo scanner control voltage affect the scanning angle (or illumination angle). According to this example, voltage changes in the galvo scanner control signal correspond to a scanning angle (i.e., illumination angle) of the illumination light, which corresponds to a location of an illumination line on the fundus of the eye. For example, at a galvo scanner voltage of 1.0 volts, the scanning angle may be 20 degrees. According to the example of FIG. 6C, a galvo scanner control signal 630 is controlled by control unit 104 to have an increasing voltage 632 over time 636 without waiting for a time delay 638. The changing voltage of the galvo scanner control signal 630 directly corresponds to a change of a scanning angle 634 (aka, illumination angle) over time 636, which determines the position of the illumination line (e.g., illumination line 204a). Detector/sensor control signals 642, 644, and 646, which start after the time delay 638, operate to capture successive rows (e.g., rows 1, 2, and 3, respectively) of the camera sensor while the scanning angle changes during time 636. A maximum value 648 of the galvo scanner control signal 630 (e.g., 1 volt) corresponds to a maximum value of scanning angle 634 (e.g., 20 degrees), while a zero voltage value 650 of the galvo scanner control signal 630 corresponds to a 0 degree scanning angle.

FIG. 7A illustrates an example of upper view control signals during narrow viewing angle dynamic viewing angle change on a galvo scanner-based imaging apparatus according to an embodiment of the invention. FIG. 7B illustrates an example of lower view control signals during narrow viewing angle dynamic viewing angle change on a galvo scanner-based imaging apparatus according to an embodiment of the invention. The examples of FIGS. 7A and 7B are similar to the examples of FIGS. 6A and 6B, respectively, except in FIGS. 7A and 7B, the images are captured with a narrow viewing angle. Thus, in the example of FIG. 7A, a galvo scanner control signal 704a increases in voltage 702a over time 706a, without waiting for a time delay 708a, while detector row number control signals 710b, 712b, and 714b operate, after the constant time delay 708a, to capture successive rows (e.g., rows 1, 2, and 3, respectively) in the camera to capture an upper view/narrow viewing angle image. In the example of FIG. 7B, galvo scanner control signal 704c increases in voltage 702c over time 706c, starting after time delay 708c, while detector row number control signals 710c, 712c, 714c, 716c, 718c, 720c, operate, without waiting for the time delay 708c, to capture a lower view/narrow viewing angle image. The time delays 708a and 708c in this example have the same duration.

FIG. 7C illustrates an example of upper view control signals during wide viewing angle dynamic viewing angle change on a galvo scanner-based imaging apparatus according to an embodiment of the invention. FIG. 7D illustrates an example of lower view control signals during wide viewing angle dynamic viewing angle change on a galvo scanner-based imaging apparatus according to an embodiment of the invention. The examples of FIGS. 7C and 7D are similar to the examples of FIGS. 7A and 7B respectively, except that in FIGS. 7C and 7D, wide viewing angle images are captured, as opposed to narrow viewing angle images in FIGS. 7A and 7B. According to the example of FIG. 7C, the galvo scanner control signal 704d is controlled by the control unit 104 to have an increasing voltage 702e over time 706d, and detector/sensor control signals 710d, 712d, and 714d, after a delay time 708b, to capture successive rows of images (e.g., rows 1, 2, and 3, respectively) to obtain an upper view/wide viewing angle image. According to the example in FIG. 7D, the galvo scanner control signal 704e increases in voltage 702g after a time delay 708d, and detector/sensor control signals 710e, 712e, 714e, 716e, 718e, and 720e are output to capture successive rows of images (e.g., rows 1-6, respectively) to obtain a lower view/wide viewing angle image.

The control unit 104 is configured to dynamically switch between capturing images according to the narrow viewing angle in FIGS. 7A and 7B, and capturing images according to the wide viewing angle in FIGS. 7C and 7D. According to an exemplary embodiment, the control unit 104 can alternate capturing narrow and wide viewing angle images after each pair of captured images.

As shown in the example of FIG. 2C, the illumination light is projected though the center of pupil plane and the backscattered light is then digitized by off-centered detector array (upper/lower or left/right), the narrow/wide is related to the field of view (FOV) of the system and it determines how wide the imaging area will be. However, the viewing angle determines stereoscopic viewing angle which is related to the depth resolution in stereoscopic imaging.

The examples of FIGS. 6A, 6B, 7A, 7B, 7C, and 7D show how the viewing angle in stereoscopic imaging can dynamically be adjusted by shortening or extending the time interval (or distance on 2D detector) from the current illumination position. The dynamic viewing angle change can be described by the following equation:

$$\theta_{view} \propto \frac{T}{M} \quad (1)$$

Where $\theta_{view}$ is a viewing angle in stereoscopic imaging, T is a relative time delay (or baseline distance in FIG. 2D) between two consecutive images (e.g., upper and lower view images), and M is an optical magnification factor. The control unit 104 adjusts the time delay T, and optical magnification factor M. For example, the constant time delay between galvo control signal and detector control signal increases, the resulting viewing angle in stereoscopic imaging also increases at a given optical magnification factor. The viewing angle change also increases or decreases depth resolution in stereoscopic image. The narrower the viewing angle, the greater the depth resolution in stereoscopic image. Alternatively, the resulting viewing angle can be decreased or increased by simply increasing or decreasing the optical magnification factor (e.g., 1×←→10×). As described further below, the viewing angle value is used for a 3D depth reconstruction process performed by the processing unit 106 according to an embodiment of the invention. M, T, and $\theta_{view}$ are managed to achieve dynamical stereoscopic imaging (i.e., to process viewing angle changes, stereoscopic imaging, 3D reconstruction/analysis/visualization, optical magnification, recording, and clinical analysis/diagnosis such as comparison with normative database and disease progression detection in near real-time). In a live eye imaging, eye motion deteriorates the quality of stereoscopic image. The dynamic stereoscopic imaging and analysis without eye motion artifacts can improve disease assessment in clinic. An eye tracking can be performed by the control unit during stereoscopic imaging. Additionally, the viewing angle can be changed by not only the optical magnification factor but also the timing (or phase shift) between the galvo control signal and the detection control signal.

FIG. 8 illustrates an example of a stereoscopic color fundus imaging apparatus including 2D camera with rolling shutter mechanism plus DMD for optical switching according to an embodiment of the invention. According to the embodiment of FIG. 8, illumination light from illumination optics 814 (part of the imaging optics 102 and also implementing the optical scanner unit 110) are output to projection optics 808 (another part of the imaging optics 102), and from the projection optics 808 to imaging optics 802 (part of the imaging optics 102) towards the eye 806. Backscattered light from the eye 806 is received by the objective lens 802c, dynamic aperture minor 802b, and relay lenses 802a in the imaging optics 802. The backscattered light from the eye is directed by the imaging optics 802 to a sensor array 804a in the camera 804 (i.e., detector/sensor unit 112). The illumination optics 804 include lenses 814a, a DMD 814b, a controllable (by the control unit 104) iris aperture 814c, and an illumination light source 814d. Also included in this embodiment are control unit 104, processing unit 106, display unit 108, and storage unit 114. As described above, the DMD 814b can be turned ON or OFF digitally (i.e., optical switching) under control from the control unit 104. In this embodiment, DMD 814d is used to control a portion of the eye that is illuminated at a given time instead of the mechanical galvo scanner used in the previously discussed embodiment. As mentioned above, DMD has a few advantages over galvo scanner such as 1) fast in response, 2) mechanically more stable compared to galvo scanner, 3) flexible illumination pattern, etc. The embodiment in FIG. 8 is configured to operate according to each of the examples shown in FIGS. 2A, 2B, 3A, 3B, 4A, and 4C. The operation is controlled according to predetermined commands stored in the storage unit 114, according to commands provided by user interface on the control unit 104 or processing unit 106, or according to commands received from a remote location by the control unit 104 or processing unit 106.

FIG. 9A illustrates an example of DMD and detector upper view control signals, and FIG. 9B illustrates an example of DMD and detector lower view control signals. When the dynamic aperture setting is in a split aperture mode, a constant time delay (e.g., time delays 910a, 910b, 1010a, 1010b, 1010c, and 1010d) between illumination and detection is zero because the viewing angle difference is introduced and controlled by switching the upper and lower view apertures. Therefore, the stereoscopic image acquisition speed is relatively faster than the aperture stop based stereoscopic imaging mode in which the time delay is greater than zero. As shown in FIG. 9A, an upper view is captured using DMD control signals 912a, 914a, 916a, 918a, 920a, and 922a which vary in voltage 902a over time 904a, without waiting for constant time delay (i.e., viewing angle) 910a, while detector/sensor control signals 924a, 926a, 928a, 930a, and 932a vary in voltage 906a, after waiting for the time delay 910a in time 904a. As shown in FIG. 9B, a lower view is captured using DMD control signals 912b, 914b, 916b, 918b, and 920b, which vary in voltage 902b after waiting for constant time delay 910b over time 904b, while detector/sensor control signals 922b, 924b, 926b, 928b, 930b, and 932b vary in voltage 906b, without waiting for time delay 910b over time 904b.

FIGS. 10A to 10D represent an example of how an embodiment of the invention may dynamically switch between narrow viewing angle capture (in FIGS. 10A and 10B) and wide viewing angle capture (in FIGS. 10C and 10D). FIG. 10A illustrates an example of upper view control signals during narrow viewing angle dynamic viewing angle change on a DMD-based imaging according to an embodiment of the invention, using DMD control signals 1012a, 1014a, 1016a, 1018a, 1020a, and 1022a, which vary in voltage 1002a over time 1004a without waiting for time delay 1010a, and detector/sensor control signals 1024a, 1026*a*, 1028*a*, 1030*a*, and 1032*a*, which vary in voltage 1006*a* over time 1004*a*, after waiting for the time delay (viewing angle) 1010*a*. FIG. 10B illustrates an example of lower view control signals during narrow viewing angle dynamic viewing angle change on a DMD-based imaging according to an embodiment of the invention, using DMD control signals 1012*b*, 1014*b*, 1016*b*, 1018*b*, and 1020*b* which vary in voltage 1002*b* over time 1004*b* after waiting for the time delay 1010*b*, and detector/sensor control signals 1022*b*, 1024*b*, 1026*b*, 1028*b*, 1030*b*, and 1032*b* vary in voltage 1006*b* over time 1004*b* without waiting for the time delay 1010*b*.

FIG. 10C illustrates an example of upper view control signals during wide viewing angle dynamic viewing angle change on a DMD-based imaging according to an embodiment of the invention, using DMD control signals 1012*c*, 1014*c*, 1016*c*, 1018*c*, 1020*c*, and 1022*c* which vary in voltage 1002*c* over time 1004*c* without waiting for time delay 1010*c*, and detector/sensor control signals 1024*c*, 1026*c*, and 1028*c* vary in voltage 1006*c* over time 1004*c* after waiting for time delay 1010*c* (which is greater than time delays 1010*a* and 1010*b*, thereby providing a wider viewing angle). FIG. 10D illustrates an example of lower view control signals during wide viewing angle dynamic viewing angle change on a DMD-based imaging according to an embodiment of the invention, using DMD control signals 1012*d*, 1014*d*, and 1016*d*, which vary in voltage 1002*d* over time 1004*d* after waiting for time delay 1010*d*, and detector/sensor control signals 1018*d*, 1020*d*, 1022*d*, 1024*d*, 1026*d*, and 1028*d* vary in voltage 1006*d* over time 1004*d* without waiting for time delay 1010*d*. These figures show how the viewing angle in stereoscopic imaging can dynamically be adjusted by shortening or extending the time interval (or distance on 2D detector) from the current illumination position. In FIGS. 10A and 10B the time delays 1010*a* and 1010*b* are the same as each other. In FIGS. 10C and 10D the time delays 1010*c* and 1010*d* are the same as each other. The time delays 1010*c* and 1010*d* are longer than the time delays 1010*a* and 1010*b*, thereby resulting in a wider viewing angle of the captured images in FIGS. 10C and 10D than in the captured images of FIGS. 10A and 10B. The acquisition and 3D reconstruction speed can be close to real-time.

FIG. 11A illustrates an example of a stereoscopic color fundus imaging apparatus including a multiple-scan camera plus galvo scanner according to an embodiment of the invention, and FIG. 11B illustrates an example of operation of the embodiment in FIG. 11A. According to the embodiment of FIG. 11A, illumination optics 1112 outputs an illumination light which is further directed by a dynamic aperture mirror 1116 towards the eye 1106. Backscattered light from the eye 1106 is received by objective lens 1112, and directed by mirror 1110 to projection optics 1108, which redirects the backscattered light to scanner 1118 (part of the optical scanner unit 110), mirror 1120, lenses 1104, dynamic aperture mirror 1116, relay lenses 1114 and ultimately to a multiple-line sensor camera 1102 which includes one or more multiple-line sensor arrays 1102*a*. The multiple-line sensor camera 1102 is part of the detector/sensor unit 112. According to this example, the projections optics 1108, which form part of imaging optics 102, includes lenses 1108*c*, mirror or DLP 1108*b*, and black dot mask 1108*a*. Also included in this embodiment are control unit 104, processing unit 106, display unit 108, and storage unit 114.

As shown by the example in FIG. 11B, the embodiment of FIG. 11A may perform a first scan (upper view) using detection line 1120 and illumination line 1122 to capture a first (upper viewing angle) color fundus image 1136. At the same time as scanning the upper view, the same camera may perform a second scan (lower view) using detection line 1134 and illumination line 1122 to capture a second (lower viewing angle) color fundus image 1138.

A multiple-line scan camera is a single camera that includes two or more line-scan detector arrays arranged in parallel. For example, a multiple-line scan camera including three rows of detector arrays can digitize the incoming backscattered light 230 at each camera trigger (i.e., for each "on/off" in FIGS. 6A-B, 7A-D, 9A-B, and 10A-C. Therefore, the overall acquisition speed may be much faster than in the first two embodiments of FIGS. 5 and 8. However, the viewing angle is fixed by the camera design in this embodiment. The multiple-line scan camera can be used to create a baseline distance (or viewing angle difference), which makes a stereoscopic imaging (or upper and lower view, left and right) possible. In this approach, the acquired images from at least two line-scanner in a multiple-scan camera should be divided into two images (FIG. 11B). The viewing angle according to this embodiment is fixed by the design of the multiple-scan camera. The overall acquisition speed is much faster than the previous two embodiments (FIGS. 5 and 8). Its control mechanism and synchronization are still important like in the previous embodiments.

FIGS. 12A, 12B, and 12C illustrate example methods of stereoscopic imaging. A stereoscopic image can be obtained using two or more images acquired with a certain different viewing angles. Two different approaches are illustrated: parallel stereo acquisition in FIG. 12A, and converging stereo acquisition in FIG. 12B. Both approaches provide comparable performance in human depth perception. In binocular stereo where the two camera axes are parallel, depth can be calculated given the disparity (the shift in position for corresponding points between the images). If the focal length of both cameras is f, the baseline b and disparity d, then the depth z is given by $z=(f \times b)/d$. In multi-baseline stereo, more than two cameras or camera locations are employed. FIG. 12C shows an example of a converging stereo acquisition approach to capture depth information in a depth direction 1210 from images of a retina 1212 of an eye 1214 through a pupil plane 1216. In this example, angle 1218 is ~+1.9 degrees and angle 1220 is ~−1.9 degrees, so the viewing angle difference may be ~3.8° between two images captured by camera 1222. If 10 μm difference in disparity 1226 is observed between two images used to produce stereo data 1224, minimum 300 μm depth resolution (assumed 1× optical magnification) can be resolved, with an illumination window 1228 of ~1.15 mm, lower detection width 1232 of ~0.36 mm, width 1230 of ~0.31 mm, and upper detection width 1234 of ~0.36 mm. The minimum depth resolution is proportional to a given optical magnification. The higher the optical magnification, the greater the resolvable depth resolution.

FIG. 13 illustrates an example of a method of stereoscopic imaging with 3D visualization and analysis processing performed using a processing unit according to an embodiment of the invention. According to this example, the method starts in step S1302, and a pair of images (e.g., upper and lower views, or left and right) obtained by the detector/sensor unit 112 are provided to the processing unit 106 in step S1304. In step S1306, disparity between the two images is estimated by registering the images from point-to-point and noting the differences at the pixel level. In step S1310, the disparity in pixels is converted to object distances (e.g., actual distance on the fundus in mm scale). In step S1308, a desired/current viewing angle is set, either by the control unit or a user interface control. The desired viewing angle may be set at any time before or during imaging, and the control unit can adjust the viewing angle to meet depth resolution requirements. Then, in step S1312, the actual depth (i.e., in a third dimension different than the two dimensions captured directly by the detector/sensor unit 112) is computed by using the equation (1) when parallel view is used or equation (2) when a converging view is used:

$$\Delta Z_{parallel} = \frac{f \times b}{d} \quad (1)$$

$$\Delta Z_{converging} = \frac{d}{SIN\theta} \quad (2)$$

where $\Delta Z_{parallel}$ is a depth in parallel view, f is a focal length, b is a baseline distance between two virtual parallel cameras (i.e., cameras resulting from an embodiment of the invention that varies the viewing angles), d is a disparity measured by point-to-point registration, viewing distance in parallel view, $\Delta Z_{converging}$ is a depth calculated by converging view, θ is a viewing angle difference between two separate images. In step S1314, clinically relevant parameters or features can be extracted from and highlighted within the calculated depth profile. For example, glaucoma and age-related macular degeneration are common causes of blindness. A volumetric analysis such as a cup volume at the optic nerve head is directly related to glaucomatous damage. Additionally, the volume change over time can be used to relate with the efficacy of clinical treatment. These types of analyses may be implemented on the processing unit. Next, the calculated depth information can be converted into a 3D map, plot, or image that can be directly visualized in step S1316, transmitted elsewhere, or stored by the storage unit 114 by step S1320 before stopping in step S1322. The operations can be repeated if not finished in step S1318.

FIG. 14A illustrates an example of stereoscopic color fundus images 1402 and 1404 captured according to an embodiment of the invention, and FIG. 14B illustrates a three dimensional plot of information plotted in three-dimensions 1406, 1408, and 1410 extracted from the stereoscopic color fundus images in FIG. 14A according to an embodiment of the invention, for example, with a field of view of about 3 mm.

FIG. 15A illustrates a three-dimensional plot of information on three-axes 1502, 1504, and 1506 depicting an estimate of cub depth 1510 resulting from a cup depth estimation performed according to an embodiment of the invention. FIG. 15B illustrates plot of information in three-dimensions 1518, 1520, and 1522 depicting a cup boundary 1512, and a disc boundary 1514, from a cup to disc ratio estimation performed according to an embodiment of the invention. To perform cup depth estimation and cup to disc ratio estimation according to an embodiment of the invention, first, a pair of stereoscopic images are acquired using the method discussed herein (e.g., upper view and lower view images). Next, point to point image registration is performed to calculate disparity (or viewing angle) between two points. Then the disparity (or angle) is used to estimate depth at each point. The resulting depth profile (Z-axis) and 2D color fundus image (X- and Y-axis) are rendered to visualize the depth information of optic nerve head.

There are a few difficulties in a stereoscopic imaging in general such as 1) eye motion during image acquisition, 2) artifacts caused imaging angle change, 3) lack of similarity between two or more images from difference views (e.g., due to moving floater in the eye), 4) long imaging time interval between two or more consecutive acquisitions (e.g., optical alignment and re-focusing needed between imaging), etc. These problems can be minimized by the embodiments disclose herein because the stereoscopic acquisition in the invention is acquired using a single camera and almost real-time. It will result in low motion artifacts on the stereoscopic color fundus image described herein. Additionally, the stereoscopic color fundus imaging method described herein can provide more reliable depth information due to higher acquisition speed.

Considering the above, the methods and system described herein improve existing stereoscopic color fundus imaging technology by at least: 1) the stereoscopic image acquisition speed; 2) improving the quality of depth profile of a given sample due to less eye motion artifacts; and 3) providing prognostic information for eye diseases such as cup depth, cup-to-disc ratio, suspicious lesion volume, etc.

FIG. 16 illustrates a block diagram of a computer that may implement the control unit 104 and/or processing unit 106 according to embodiments described herein.

Control aspects of the present disclosure may be embodied as a system, a method, and/or a computer program product. The computer program product may include a computer readable storage medium on which computer readable program instructions are recorded that may cause one or more processors to carry out aspects of the embodiment.

The computer readable storage medium may be a tangible device that can store instructions for use by an instruction execution device (processor). The computer readable storage medium may be, for example, but is not limited to, an electronic storage device, a magnetic storage device, an optical storage device, an electro-magnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electro-magnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or computer server, or any combination of these computing devices. The remote computer or computer server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 16 further illustrates a networked system of one or more networked computers and servers. In an embodiment, the hardware and software environment illustrated in FIG. 16 may provide an exemplary platform for implementation of the software and/or methods according to the present disclosure.

Referring to FIG. 16, a networked system may include, but is not limited to, computer 1605, network 1610, remote computer 1615, web server 1620, cloud storage server 1625 and computer server 1630. In some embodiments, multiple instances of one or more of the functional blocks illustrated in FIG. 16 may be employed.

Additional details of computer 1605 are shown in FIG. 16. The functional blocks illustrated within computer 1605 are provided only to establish exemplary functionality and are not intended to be exhaustive. And while details are not provided for remote computer 1615, web server 1620, cloud storage server 1625 and computer server 1630, these other computers and devices may include similar functionality to that shown for computer 1605.

Computer 1605 may be a personal computer (PC), a desktop computer, laptop computer, tablet computer, netbook computer, a personal digital assistant (PDA), a smart phone, or any other programmable electronic device capable of communicating with other devices on network 1610.

Computer 1605 may include processor 1635, bus 1637, memory 1640, non-volatile storage 1645, network interface 1650, peripheral interface 1655 and display interface 1665. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 1635 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 1637 may be a proprietary or industry standard high-speed parallel or serial peripheral interconnect bus, such as ISA, PCI, PCI Express (PCI-e), AGP, and the like.

Memory 1640 and non-volatile storage 1645 may be computer-readable storage media. Memory 1640 may include any suitable volatile storage devices such as Dynamic Random-Access Memory (DRAM) and Static Random-Access Memory (SRAM). Non-volatile storage 1645 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 1648 may be a collection of machine-readable instructions and/or data that is stored in non-volatile storage 1645 and is used to create, manage and control certain software functions that are discussed in detail elsewhere in the present disclosure and illustrated in the drawings. In some embodiments, memory 1640 may be considerably faster than non-volatile storage 1645. In such embodiments, program 1648 may be transferred from non-volatile storage 1645 to memory 1640 prior to execution by processor 1635.

Computer 1605 may be capable of communicating and interacting with other computers via network 1610 through network interface 1650. Network 1610 may be, for example, a local area network (LAN), a wide area network (WAN) such as the Internet, or a combination of the two, and may include wired, wireless, or fiber optic connections. In general, network 1610 can be any combination of connections and protocols that support communications between two or more computers and related devices.

Peripheral interface 1655 may allow for input and output of data with other devices that may be connected locally with computer 1605. For example, peripheral interface 1655 may provide a connection to external devices 1660. External devices 1660 may include devices such as a keyboard, a mouse, a keypad, a touch screen, and/or other suitable input devices. External devices 1660 may also include portable computer-readable storage media such as, for example, thumb drives, portable optical or magnetic disks, and memory cards. Software and data used to practice embodiments of the present disclosure, for example, program 1648, may be stored on such portable computer-readable storage media. In such embodiments, software may be loaded onto non-volatile storage 1645 or, alternatively, directly into memory 1640 via peripheral interface 1655. Peripheral interface 1655 may use an industry standard connection, such as RS-232 or Universal Serial Bus (USB), to connect with external devices 1660.

Display interface 1665 may connect computer 1605 to display 1670. Display 1670 may be used, in some embodiments, to present a command line or graphical user interface to a user of computer 1605. Display interface 1665 may connect to display 1670 using one or more proprietary or industry standard connections, such as VGA, DVI, DisplayPort and HDMI.

As described above, network interface 1650, provides for communications with other computing and storage systems or devices external to computer 1605. Software programs and data discussed herein may be downloaded from, for example, remote computer 1615, web server 1620, cloud storage server 1625 and computer server 1630 to non-volatile storage 1645 through network interface 1650 and network 1610. Furthermore, the systems and methods described in this disclosure may be executed by one or more computers connected to computer 1605 through network interface 1650 and network 1610. For example, in some embodiments the systems and methods described in this disclosure may be executed by remote computer 1615, computer server 1630, or a combination of the interconnected computers on network 1610.

Data, datasets and/or databases employed in embodiments of the systems and methods described in this disclosure may be stored and or downloaded from remote computer 1615, web server 1620, cloud storage server 1625 and computer server 1630.

Obviously, numerous modifications and variations of the present invention are possible in light of the above teachings. It is therefore to be understood that within the scope of the appended claims, the invention may be practiced otherwise than as specifically described herein.

The invention claimed is:

1. An ophthalmological imaging device comprising:
   illumination optics including an illumination light source configured to output an illumination light;
   a scanner configured to receive the illumination light from the illumination optics, and redirect the illumination light toward a portion of an object to be imaged;
   an optical image capture device including a camera configured to receive backscattered light that is scattered from the illumination light by the object and capture first and second images of the backscattered light;
   a control processor configured to control the scanner and the optical image capture device to cause the optical image capture device to capture the first and second images of the object, the first and second images being captured by the camera at different times and extracted from different portions of the backscattered light; and
   an image processor configured to generate a stereoscopic image from the first and second images of the object, wherein
   the control processor is configured to control the scanner and the optical image capture device to cause the optical image capture device to capture the first image to include a first portion of the backscattered light, and to capture the second image to include a second portion of the backscattered light;
   the first portion of the backscattered light is received by the optical image capture device along a first backscattering angle and the second portion of the backscattered light is received by the optical image capture device along a second backscattering angle that is different from the first backscattering angle by a viewing angle difference;
   the optical image capture device is further controllable to vary an optical magnification factor of the captured image; and
   the control processor varies the viewing angle difference by controlling the optical magnification factor of the optical image capture device and a timing of a row number capture signal to cause the first and second images to be captured.

2. The device according to claim 1, wherein the scanner includes one of a galvo mechanical scanner, a digital micromirror device (DMD), and a polygon scanner.

3. The device according to claim 1, wherein the control processor is further configured to control a timing of a row number capture signal and a galvo scanner voltage control signal to cause the first and second images to be captured.

4. The device according to claim 3, wherein the row number capture signal indicates a timing of capture by a designated one or more rows of pixels in a plurality of rows of pixels in a sensor array in the camera.

5. The device according to claim 3, wherein the galvo scanner voltage control signal controls a deflection angle of light deflected by the galvo scanner mirror, the voltage of the galvo scanner voltage control signal controlled to vary from a negative voltage to a positive voltage.

6. The device according to claim 1, wherein
   the control processor controls the scanner and the optical image capture device to cause the optical image capture device to capture the third and fourth images of the object;
   the control processor varies a field of view angle between the third image and the fourth image by controlling the optical magnification factor of the optical image capture device; and
   the control processor controls the viewing angle difference between the first and second images to be the same as a viewing angle difference between the third and fourth images.

7. The device according to claim 6, wherein
   the optical image capture device includes an actuator controlling a position of an optical magnifier to vary the optical magnification factor of the captured image.

8. The device according to claim 1, wherein the object is a fundus of an eye.

9. The device according to claim 1, wherein
   the control processor is configured to control the scanner and the optical image capture device to cause the optical image capture device to capture the first image to have a first viewing angle, and
   the control processor controls the first viewing angle based on a time delay between a control signal for the optical image capture device and a control signal for the scanner.

10. The device according to claim 1, wherein the first portion of the backscattered light is received at a first scattering angle from the object, and the second portion of the backscattered light is received from a second scattering angle from the object that is separated from the first scattering angle by 180 degrees.

11. The device according to claim 1, wherein the control processor is further configured to change a capturing order of the first and second images.

12. The device according to claim 1, wherein the control processor is further configured to control the scanner and the optical image capture device to cause the optical image capture device to capture the first image of the object at a first viewing angle and the second image of the object at a second viewing angle that is different from the first viewing angle.

13. The device according to claim 1, wherein the control processor is further configured to control at least one of the illumination optics, the scanner, and the optical image capture device to capture the first and second images of the object so that a field of view angle in the first image is the same as a field of view angle in the second image.

14. The device according to claim 1, wherein the control processor is further configured to control at least one of the illumination optics, the scanner, and the optical image capture device to capture third and fourth images having different viewing angles from each other, a same field of view angle as each other, and a different field of view angle from the field of view angle of the first and second images.

15. The device according to claim 1, wherein the image processor is further configured to generate information for a 3D visualization, a depth profile, a volume quantification, a disease progression, and a normative database for a critical diagnosis.

16. The device according to claim 1, wherein the control processor is configured to control the scanner and the optical image capture device to cause the optical image capture device to capture the first and second images of the object to be extracted from different portions of the backscattered light based by using a differently configured aperture during each of the first and second images.

17. The device according to claim 16, further comprising:
a horizontal aperture in an optical path of the backscattered light; and
the control processor is further configured to dynamically switch the horizontal aperture between illuminating an upper portion of the object when capturing one of the first and second image of the object, and illuminating a lower portion of the object when capturing the other of the first and second image of the object.

18. The device according to claim 16, further comprising:
a vertical aperture in an optical path of the backscattered light; and
the control processor is further configured to dynamically switch the vertical aperture between illuminating a left portion of the object when capturing one of the first and second image of the object, and illuminating a right portion of the object when capturing the other of the first and second image of the object.

19. A method of operating an ophthalmological imaging device, the method comprising:
outputting an illumination light;
receiving the illumination light;
redirecting an optical axis of the illumination light toward a portion of an object to be imaged;
receiving backscattered light that is scattered from the illumination light by the object;
capturing first and second images of the backscattered light by a same image capture device at different times and extracted from different portions of the backscattered light;
generating a stereoscopic image from the first and second images of the object;
the capturing the first image includes capturing a first portion of the backscattered light. and the capturing the second image includes capturing a second portion of the backscattered light;
receiving the first portion of the backscattered light along a first backscattering angle;
receiving the second portion of the backscattered light along a second backscattering angle that is different from the first backscattering angle by a viewing angle difference;
controllably varying an optical magnification factor of the captured image; and
varying the viewing angle difference by controlling the optical magnification factor and a timing of a row number capture signal to cause the first and second images to be captured.

20. The method according to claim 19, further comprising:
redirecting the optical axis of the illumination light with one of a galvo mechanical scanner, a digital micromirror device (DMD), and a polygon scanner.

21. The method according to claim 19, further comprising:
controlling a timing of a row number capture signal and a galvo scanner voltage control signal to cause the first and second images to be captured.

22. The method according to claim 19, further comprising:
controlling the row number capture signal to indicate a timing of capture by a designated one or more rows of pixels in a plurality of rows of pixels in a sensor array in the image capture device.

23. The method according to claim 21, further comprising:
controlling the galvo scanner voltage control signal to vary a deflection angle of light deflected by the galvo scanner mirror, with the voltage of the galvo scanner voltage control signal being varied from a negative voltage to a positive voltage.

24. The method according to claim 19, further comprising:
capturing a third image of the object;
capturing a fourth image of the object;
changing a field of view angle between the third image and the fourth image by controlling the optical magnification factor of the optical image capture device; and
controlling the viewing angle difference between the first and second images to be the same as a viewing angle difference between the third and fourth images.

25. The method according to claim 24, further comprising:
controlling an actuator to change a position of an optical magnifier to vary the optical magnification factor of the captured image.

26. The method according to claim 19, wherein the object is a fundus of an eye.

27. The method according to claim 19, further comprising:
capturing the first image to have a first viewing angle; and
controlling the first viewing angle based on a time delay between a control signal for an optical image capture device and a control signal for a scanner.

28. The method according to claim 19, wherein the first portion of the backscattered light is received at a first scattering angle from the object, and the second portion of the backscattered light is received from a second scattering angle from the object that is separated from the first scattering angle by 180 degrees.

29. The method according to claim 19, further comprising:
changing a capturing order of the first and second images.

30. The method according to claim 19, further comprising:
capturing the first image of the object at a first viewing angle and the second image of the object at a second viewing angle that is different from the first viewing angle.

31. The method according to claim 19, further comprising:
capturing the first and second images of the object so that a field of view angle in the first image is the same as a field of view angle in the second image.

32. The method according to claim 19, further comprising:
capturing third and fourth images having different viewing angles from each other, a same field of view angle as each other, and a different field of view angle from the field of view angle of the first and second images.

33. The method according to claim 19, further comprising:
generating information for a 3D visualization, a depth profile, a volume quantification, a disease progression, and a normative database for a critical diagnosis.

34. The method according to claim 19, further comprising:
capturing the first and second images of the object to be extracted from different portions of the backscattered light based by using a differently configured aperture during each of the first and second images.

35. The method according to claim 19, further comprising:
arranging a horizontal aperture in an optical path of the backscattered light; and
dynamically switch the horizontal aperture between illuminating an upper portion of the object when capturing one of the first and second image of the object, and illuminating a lower portion of the object when capturing the other of the first and second image of the object.

36. The method according to claim 19, further comprising:
arranging a vertical aperture in an optical path of the backscattered light; and
dynamically switching the vertical aperture between illuminating a left portion of the object when capturing one of the first and second image of the object, and illuminating a right portion of the object when capturing the other of the first and second image of the object.

37. A non-tangible computer readable medium storing a computer program, which when executed by a computer, causes the computer to perform steps of operating an ophthalmological imaging device, the steps comprising:
outputting an illumination light;
receiving the illumination light;
redirecting the illumination light toward a portion of an object to be imaged;
receiving backscattered light that is scattered from the illumination light by the object;
capturing first and second images of the backscattered light by a same image capture device at different times and extracted from different portions of the backscattered light;
generating a stereoscopic image from the first and second images of the object;
the capturing the first image includes capturing a first portion of the backscattered light. and the capturing the second image includes capturing a second portion of the backscattered light;
receiving the first portion of the backscattered light along a first backscattering angle;
receiving the second portion of the backscattered light along a second backscattering angle that is different from the first backscattering angle by a viewing angle difference;
controllably varying an optical magnification factor of the captured image; and
varying the viewing angle difference by controlling the optical magnification factor and a timing of a row number capture signal to cause the first and second images to be captured.

* * * * *